(12) United States Patent
Qin et al.

(10) Patent No.: US 8,957,039 B2
(45) Date of Patent: Feb. 17, 2015

(54) METHODS AND COMPOSITIONS FOR THE DIAGNOSIS AND PROGNOSIS OF CERVICAL INTRAEPITHELIAL NEOPLASIA AND CERVICAL CANCER

(75) Inventors: Wenyan Qin, Beijing (CN); Peng Dong, Beijing (CN); Tuo Deng, Beijing (CN); Cailing Ma, Beijing (CN); Keith Richard Mitchelson, St. Lucia (AU); Hao Wen, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 13/389,428

(22) PCT Filed: Aug. 6, 2010

(86) PCT No.: PCT/CN2010/001202
§ 371 (c)(1),
(2), (4) Date: Apr. 20, 2012

(87) PCT Pub. No.: WO2011/015040
PCT Pub. Date: Feb. 10, 2011

(65) Prior Publication Data
US 2012/0202872 A1 Aug. 9, 2012

(30) Foreign Application Priority Data

Aug. 7, 2009 (CN) .................. PCT/CN2009/000895

(51) Int. Cl.
*C12N 15/11* (2006.01)
*C40B 40/06* (2006.01)
*C12Q 1/68* (2006.01)

(52) U.S. Cl.
CPC ........ *C12Q 1/6886* (2013.01); *C12Q 2600/118* (2013.01); *C12Q 2600/136* (2013.01); *C12Q 2600/158* (2013.01); *C12Q 2600/178* (2013.01)
USPC ......................................... 514/44 A; 506/16

(58) Field of Classification Search
None
See application file for complete search history.

(56) References Cited

U.S. PATENT DOCUMENTS

2005/0277139 A1* 12/2005 Bentwich et al. ................ 435/6

FOREIGN PATENT DOCUMENTS

| WO | WO 2005056797 A1 * | 6/2005 |
| WO | WO-2005/118806 | 12/2005 |
| WO | WO 2008061537 A2 * | 5/2008 |
| WO | WO-2008/095096 | 8/2008 |
| WO | WO-2009/036332 | 3/2009 |
| WO | WO 2009036332 A1 * | 3/2009 |

OTHER PUBLICATIONS

Korpal et al, The miR-200 Family Inhibits Epithelial-Mesenchymal Transition and Cancer Cell Migration by Direct Targeting of E-cadherin Transcriptional Repressors ZEB1 and ZEB2, 2008, 283: 14910-14914.*
Response to European Search Report for EP Application No. 10805944.5, filed Jun. 28, 2013, 12 pages.
Communication pursuant to Article 94(3) EPC for EP 10805944.5, mailed Jun. 5, 2014, 7 pages.
Bandres et al., "Identification by Real-time PCR of 13 mature microRNAs differentially expressed in colorectal cancer and non-tumoral tissues" Mol. Cancer (2006) 5:29.
Budha et al., "Identification of metastasis-related microRNAs in hepatocellular carcinoma" Hepatology (2008) 47:897-907.
Burk, "Pernicious papillomavirus infection" N. Engl. J. Med. (1999) 341:1687-1688.
Calin et al., "Human microRNA genes are frequently located at fragile sites and genomic regions involved in cancers" Proc. Natl. Acad. Sci. USA (2004) 101:2999-3004.
Chen, "MicroRNAs as oncogenes and tumor suppressors" N. Engl. J. Med. (2005) 353:1768-1771.
Fatica et al., "MicroRNAs and hematopoietic differentiation" Cold Spring Harb. Symp. Quant. Biol. (2006) 71:205-210.
Guo et al., "Distinctive microRNA profiles relating to patient survival in esophageal squamous cell carcinoma" Cancer Res. (2008) 68:26-33.
He et al., "A microRNA component of the p53 tumour suppressor network" Nature (2007) 447:1130-1134.
Hwang and Mendell, "MicroRNAs in cell proliferation, cell death, and tumorigenesis" Br. J. Cancer (2006) 94:776-780.
Lee et al., "Altered microRNA expression in cervical carcinomas" Clin. Cancer Res. (2008) 14: 2535-2542.
Lewis and Bartel, "Conserved seed pairing, often flanked by adenosines, indicates that thousands of human genes are microRNA targets" Cell (2005) 120:15-20.
Lewis et al., "Prediction of mammalian microRNA targets" Cell (2003) 115:787-798.
Ma et al., "Tumour invasion and metastasis initiated by microRNA-10b in breast cancer" Nature (2007) 449:682-688.
Marshall and Hodgson, "DNA chips: an array of possibilities" Nature Biotechnol. (1998) 16:27-31.
Matson et al., "Biopolymer synthesis on polypropylene supports: oligonucleotide arrays" Anal. Biochem. (1995) 224(1):110-6.
Parkin et al., "Global cancer statistics, 2002" CA Cancer J. Clin. (2005) 55:74-108.

(Continued)

*Primary Examiner* — Tracy Vivlemore
*Assistant Examiner* — Kate Poliakova
(74) *Attorney, Agent, or Firm* — Morrison & Foerster LLP

(57) ABSTRACT

The invention provides methods and compositions for the diagnosis and prognosis of cervical intraepithelial neoplasia and cervical cancer. The methods comprise the step of determining the expression levels or genetic status of specific miRNAs.

24 Claims, 5 Drawing Sheets

(56) References Cited

OTHER PUBLICATIONS

Ramsay, "DNA Chips: state-of-the-art" Nature Biotechnol. (1998) 16:40-44.
Scheffner et al., "The E6 oncoprotein encoded by human papillomavirus types 16 and 18 promotes the degradation of p53" Cell (1990) 63:1129-1136.
Schena et al., "Parallel human genome analysis: Microarray-based expression monitoring of 1000 genes" PNAS USA (1996) 93:10614-10619.
Szafranska et al., "MicroRNA expression alterations are linked to tumorigenesis and non-neoplastic processes in pancreatic ductal adenocarcinoma" Oncogene (2007) 26:4442-4452.
Varnholt et al., "MicroRNA gene expression profile of hepatitis C virus-associated hepatocellular carcinoma" Hepatology (2008) 47:1223-1232.
Voorhoeve et al., "A genetic screen implicates miRNA-372 and miRNA-373 as oncogenes in testicular germ cell tumors" Cell (2006) 124:1169-1181.
Wang et al., "Aberrant expression of oncogenic and tumor-suppressive microRNAs in cervical cancer is required for cancer cell growth" PLoS One (2008) 3:e2557.
Wong et al., "Identification of pyruvate kinase type M2 as potential oncoprotein in squamous cell carcinoma of tongue through microRNA profiling" Int. J. Cancer (2008) 123:251-257.
Yekta et al., "MicroRNA-directed cleavage of HOXB8 mRNA" Science (2004) 304:594-596.
Zur Hausen, "Papillomaviruses and cancer: from basic studies to clinical application" Nat. Rev. Cancer (2002) 2:342-350.
Blanchard, et al., Biosensors & Bioelectronics, 11:687-690, (1996).
Maskos and Southern, Nucleic. Acids. Res. (1992), 20:1679-1684.
Griffths-Jones, et al., Nucleic Acids Research, 2006, vol. 34, Database issue.
Einat, Methods Mol. Biol. (2006), 342:139-157.
Thompson, et al., Genes Dev. (2006), 20:2202-2207.
Matteucci et al., J. Am. Chem. Soc., 3:3185-3191 (1981).
Shaw et al., Nucleic Acids Res., 19:747 (1991).
Milligan et al., J. Med. Chem., 36:1923 (1993).
International Search Report for PCT/CN2010/001202, mailed on Nov. 18, 2010.
International Preliminary Report on Patentability for PCT/CN2010/001202, issued on Feb. 7, 2012.
European Search Report for EP Application No. 10805944.5-1222 / 2463381, issued Nov. 29, 2012, 13 pages.
Lui Weng-Onn et al., "Patterns of known and novel small RNAs in human cervical cancer" Cancer Research (2007) 67(13):6031-6043.

* cited by examiner

METHODS AND COMPOSITIONS FOR THE DIAGNOSIS AND PROGNOSIS OF CERVICAL INTRAEPITHELIAL NEOPLASIA AND CERVICAL CANCER

CROSS-REFERENCE TO RELATED APPLICATIONS

This application is the national phase of PCT application PCT/CN2010/001202 having an international filing date of Aug. 6, 2010, which claims priority to PCT/CN2009/000895 filed Aug. 7, 2009. The contents of the above-listed PCT applications are incorporated herein by this reference in their entireties.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 514572006400Seqlist.txt | Mar. 15, 2012 | 5,703 bytes |

TECHNICAL FIELD

This application pertains to systems and methods for diagnosis of disease (such as cervical dysplasia and cervical cancer), prognosis and improvement of patient survival based on the expression level of microRNAs.

BACKGROUND ART

Uterine cervical cancer is the second most common cancer among women worldwide, with nearly 500,000 new cases per year (Parkin et al., 2005). It caused an estimated 274,000 deaths in the year 2002 and it is one of the leading causes of cancer-related deaths in young women (zur Hausen, 2002). Cervical cancer typically results from cellular transformation after persistent infections with high-risk type human papilloma virus (HPV) (Scheffner et al., 1990). Almost all squamous cell carcinomas and the majority of adenocarcinomas of the stratified epithelium are HPV positive. Although HPV is capable of initiating cancer through the disruption of multiple tumor-suppressor pathways, alone it is not sufficient for the development of the fully transformed cancer phenotype (Burk, 1999). Additional host factors are required for the development of the malignant phenotype.

A precursor of cervical cancer is also called cervical dysplasia, which literally means abnormal cell growth. There are two different systems for classifying cervical dysplasia, the SIL (squamous intraepithelial lesion) system and the CIN (cervical intraepithelial neoplasia) system. Although what the systems describe is similar, they differ in some important respects. The SIL system looks only at individual cells, generally from a Pap test, and these cells are classified according to the degree of cell abnormality. According to the SIL system, cervical dysplasia is divided into AGUS or AGCUS (atypical glandular cells of undetermined significance), LSIL (low grade squamous intraepithelial lesion) and HSIL (high grade squamous intraepithelial lesion). In the CIN system, classification of cervical dysplasia is based both on the degree of dysplasia within the individual cells and the depth below the surface of the cervix to which the dysplasia extends. According to the CIN system, cervical dysplasia is divided into CIN1 (corresponding to mild dysplasia or LSIL), CIN2 (corresponding to moderate dysplasia or HSIL) and CIN3 (corresponding to severe dysplasia or HSIL). Most of CIN1 will regress back to normal tissue over time but about 11% of CIN1 will progress to CIN3. Only a very small percentage of CIN1 leads to cancer. About 43% of CIN2 will regress back to normal and 20% will progress to CIN3. Although some CIN3 will spontaneously regress, this dysplasia is almost always treated since the next step is cancer. CIN3 is sometimes also referred to as carcinoma in situ (CIS).

Three methods are widely used for the screening of cervical cancer and cervical dysplasia, cytology screening, visual inspection with acetic acid application (VIA) and HPV tests. Currently, no method is available to distinguish progressive CIN from that destined to regress. The over-treatment of screen positive women is common.

MicroRNAs (miRNAs) are species of small non-coding single-stranded regulatory RNAs that interact with the 3'-untranslated region (3'-UTR) of target mRNA molecules through partial sequence homology (Yekta et al., 2004). They participate in regulatory networks as controlling elements that direct comprehensive gene expression (Fatica et al., 2006). Bioinformatics analysis has predicted that a single miRNA can regulate hundreds of target genes, contributing to the combinational and subtle regulation of numerous genetic pathways (Hwang and Mendell, 2006; Lewis et al., 2005).

Altered levels of expression of miRNAs correlate with various cancers and the individual controlling elements are thought capable to act as either oncogenes or tumor suppressors (Chen, 2005). A global study on the distribution of miRNAs in human genome revealed that 50% of the annotated miRNA genes are located in the cancer-associated genomic regions known as "fragile sites" (Calin et al., 2004). Furthermore, numerous functional studies indicate that different miRNAs have distinct effects at different stages of cancer progression, from tumorigenesis (He et al., 2007; Voorhoeve et al., 2006) to cancer invasion and metastasis (Budhu et al., 2008; Ma et al., 2007). The deregulation of miRNA levels has been reported in cervical cancer (Lee et al., 2008; Wang et al., 2008), but the effects of individual deregulated miRNA species in cervical cancer are largely unexplored.

Deregulation of miR-133 has also been reported in a number of other diseases, including colorectal carcinoma (Bandres et al., 2006), tongue squamous cell carcinoma (Wong et al., 2008), esophageal squamous cell carcinoma (Guo et al., 2008) and pancreatic ductal adenocarcinoma (Szafranska et al., 2007).

The disclosures of all publications, patents, patent applications and published patent applications referred to herein are hereby incorporated herein by reference in their entireties.

SUMMARY OF THE INVENTION

The present invention provides a system for determining the level of miRNA expression, which system comprises a plurality of probes, wherein at least about 50% of the probes are capable of detecting an miRNA having a nucleotide sequence that is set forth in SEQ ID NO:1-20 or their corresponding homologues. Also provided are methods for cancer diagnosis and prognosis, particularly cervical dysplasia and cervical cancer diagnosis and prognosis, based on the expression levels of miRNAs or the genetic status of corresponding miRNA genes. Further provided are pharmaceutical compositions and methods of treatment for cervical dysplasia and cervical cancer comprising an agent that alters the expression level of at least one miRNA having a nucleotide sequence that is set forth in SEQ ID NO:1-20 or their corresponding homologues, and a pharmaceutically acceptable carrier.

Accordingly, in one aspect, the present invention provides a system for determining the level of miRNA expression, which system comprises a plurality of probes, wherein at least about 50% of the probes are capable of detecting an miRNA having a nucleotide sequence that is set forth in SEQ ID NO:1-20 or their corresponding homologues. In one embodiment, at least about 50% of the probes are capable of detecting at least five miRNAs having a nucleotide sequence that is set forth in SEQ ID NO:1-20 or their corresponding homologues. In another embodiment, at least about 50% of the probes are capable of detecting at least ten miRNAs having a nucleotide sequence that is set forth in SEQ ID NO:1-20 or their corresponding homologues. In yet another embodiment, at least about 50% of the probes are capable of detecting an miRNA having a nucleotide sequence that is set forth in SEQ ID NO:1-13 or their corresponding homologues, and an miRNA having a nucleotide sequence that is set forth in SEQ ID NO:14-20 or their corresponding homologues. In still yet another embodiment, at least about 50% of the probes are capable of detecting all miRNAs having a nucleotide sequence that is set forth in SEQ ID NO:1-20 or their corresponding homologues.

In some embodiments, the expression level of at least one (including for example at least any of 2, 3, 5, 10, 13) miRNA having a nucleotide sequence that is set forth in SEQ ID NO:1-13 or their corresponding homologues are determined In some embodiments, the levels of at least one (including for example at least any of 2, 3, 5, 7) miRNA having a nucleotide sequence that is set forth in SEQ ID NO:14-20 or their corresponding homologues are determined. In some embodiments, the levels of at least one (including for example at least any of 2, 3, 5, 10, 13) miRNA having a nucleotide sequence that is set forth in SEQ ID NO:1-13 or their corresponding homologues and at least one (including for example at least any of 2, 3, 5, 7) miRNA having a nucleotide sequence that is set forth in SEQ ID NO:14-20 or their corresponding homologues are determined.

In some embodiments, at least about 15% (including for example at least about any of 20%, 30%, 40%, 50%, 60%, 70%, 80%, 90%, or 95%) of the probes are capable of detecting an miRNA having a nucleotide sequence that is set forth in SEQ ID NO:1-20 or their corresponding homologues. In some embodiments, the system comprises at least one (including for example at least any of 2, 5, 10, 15, 20, 25, 30, 35, and 40) probe that is capable of detecting an miRNA having a nucleotide sequence that is set forth in SEQ ID NO:1-20 or their corresponding homologues.

In some embodiments, at least one of the miRNA comprises hsa-miR-133b or its corresponding homologues. In some embodiments, the miRNA comprises hsa-miR-133a, hsa-miR-133b, hsa-miR-140-3p, hsa-miR-143*, hsa-miR-145, hsa-miR-223, hsa-miR-99b, hsa-miR-221, hsa-miR-320a, hsa-miR-100, hsa-miR-199a-5p, hsa-miR-127-3p, hsa-miR-214, or their corresponding homologues. In some embodiments, the miRNA comprises hsa-miR-203, hsa-miR-190, hsa-miR-200b, hsa-miR-200c, hsa-miR-200a, hsa-miR-31, hsa-miR-141, or their corresponding homologues.

In some embodiments, the system contains 20 probes. The sequences of the 20 probes may be designed as a) or b): a) complementary sequences to the nucleotide sequences that are set forth in SEQ ID NO:1-20; b) additional 10-30 polyT sequences (for example, an oligonucleotide sequence containing 19 polyT) linked to the probes of a).

In another aspect, the present invention provides a method for testing a sample for cervical cancer or cervical dysplasia, which method comprises: a) determining the level of miRNA expression in the sample using a system comprising a plurality of probes, wherein at least about 50% of the probes are capable of detecting an miRNA having a nucleotide sequence that is set forth in SEQ ID NO:1-20 or their corresponding homologues; b) comparing the level of miRNA expression with a reference level; and c) classifying the sample as cancerous or dysplastic if the sample exhibits a characteristic change in the level of miRNA expression.

In one embodiment, the characteristic change in the level of miRNA expression comprises a substantial increase in the level of at least one miRNA having a nucleotide sequence that is set forth in SEQ ID NO:1-13 or their corresponding homologues. In another embodiment, the characteristic change in the level of miRNA expression comprises a substantial increase in the level of hsa-miR-133b or its corresponding homologues. In yet another embodiment, the characteristic change in the level of miRNA expression comprises a substantial decrease in the level of at least one miRNA having a nucleotide sequence that is set forth in SEQ ID NO:14-20 or their corresponding homologues.

In a further embodiment, the characteristic change in the level of miRNA expression comprises a substantial increase in the level of at least one miRNA having a nucleotide sequence that is set forth in SEQ ID NO:1-13 or their corresponding homologues, and a substantial decrease in the level of at least one miRNA having a nucleotide sequence that is set forth in SEQ ID NO:14-20 or their corresponding homologues. In another embodiment, the characteristic change in the level of miRNA expression comprises a substantial increase in the level of at least three miRNAs having a nucleotide sequence that is set forth in SEQ ID NO:1-13 or their corresponding homologues, and a substantial decrease in the level of at least three miRNAs having a nucleotide sequence that is set forth in SEQ ID NO:14-20 or their corresponding homologues. In yet another embodiment, the characteristic change in the level of miRNA expression comprises a substantial increase in the level of at least five miRNAs having a nucleotide sequence that is set forth in SEQ ID NO:1-13 or their corresponding homologues, and a substantial decrease in the level of at least five miRNAs having a nucleotide sequence that is set forth in SEQ ID NO:14-20 or their corresponding homologues. In some embodiments, the characteristic change in the level of miRNA expression comprises a substantial increase in the level of all miRNAs having a nucleotide sequence that is set forth in SEQ ID NO:1-13 or their corresponding homologues, and a substantial decrease in the level of all miRNAs having a nucleotide sequence that is set forth in SEQ ID NO:14-20 or their corresponding homologues.

Also provided herein is a method for testing a sample for cervical cancer or cervical dysplasia, which method comprises determining the genetic status of at least one miRNA in the sample using the system comprising a plurality of probes, wherein at least about 50% of the probes are capable of detecting an miRNA having a nucleotide sequence that is set forth in SEQ ID NO:1-20 or their corresponding homologues, wherein a characteristic change in the genetic status of the miRNA indicates the sample as cancerous or dysplastic. In one embodiment, the characteristic change in the genetic status of miRNA comprises an amplification of at least one miRNA having a nucleotide sequence that is set forth in SEQ ID NO:1-13 or their corresponding homologues. In another embodiment, the characteristic change in the genetic status of miRNA comprises an amplification of hsa-miR-133b or its corresponding homologues. In yet another embodiment, the characteristic change in the genetic status of miRNA comprises a deletion of at least one miRNA having a nucleotide sequence that is set forth in SEQ ID NO:14-20 or their corresponding homologues.

In a further embodiment, the characteristic change in the genetic status of miRNA comprises an amplification of at least one miRNA having a nucleotide sequence that is set forth in SEQ ID NO:1-13 or their corresponding homologues, and a deletion of at least one miRNA having a nucleotide sequence that is set forth in SEQ ID NO:14-20 or their corresponding homologues. In another embodiment, the characteristic change in the genetic status of miRNA comprises an amplification of at least three miRNAs having a nucleotide sequence that is set forth in SEQ ID NO:1-13 or their corresponding homologues, and a deletion of at least three miRNAs having a nucleotide sequence that is set forth in SEQ ID NO:14-20 or their corresponding homologues. In yet another embodiment, the characteristic change in the genetic status of miRNA comprises an amplification of at least five miRNAs having a nucleotide sequence that is set forth in SEQ ID NO:1-13 or their corresponding homologues, and a deletion of at least five miRNAs having a nucleotide sequence that is set forth in SEQ ID NO:14-20 or their corresponding homologues.

In another aspect, the present invention provides a method for diagnosing cervical cancer or cervical dysplasia in an individual, which method comprises determining a characteristic change in the level of miRNA expression in a sample from the individual using the method for testing a sample for cervical cancer or cervical dysplasia, which method comprises: a) determining the level of miRNA expression in the sample using the system comprising a plurality of probes, wherein at least about 50% of the probes are capable of detecting an miRNA having a nucleotide sequence that is set forth in SEQ ID NO:1-20 or their corresponding homologues; b) comparing the level of miRNA expression with a reference level, and c) classifying the sample as cancerous or dysplastic if the sample exhibits a characteristic change in the level of miRNA expression.

Further provided herein is a method for diagnosing cervical cancer or cervical dysplasia in an individual, which method comprises determining the genetic status of miRNA in a sample from the individual using the method for testing a sample for cervical cancer or cervical dysplasia, which method comprises determining the genetic status of at least one miRNA in the sample using the system comprising a plurality of probes, wherein at least about 50% of the probes are capable of detecting an miRNA having a nucleotide sequence that is set forth in SEQ ID NO:1-20 or their corresponding homologues, wherein a characteristic change in the genetic status of the miRNA indicates the sample as cancerous or dysplastic.

In another aspect, the present invention provides a method of prognosis for survival for an individual having cervical cancer or cervical dysplasia, which method comprises: a) determining the level of miRNA expression in the sample using a system comprising a plurality of probes, wherein at least about 50% of the probes are capable of detecting an miRNA having a nucleotide sequence that is set forth in SEQ ID NO:1-20 or their corresponding homologues; and b) comparing the level of miRNA expression with a reference level, wherein a characteristic change in the level of miRNA expression indicates a high or low rate of survival for the individual. In some embodiments, the method further comprises determining a proper course of treatment for the individual.

Also provided herein is a method for prognosis of an individual having cervical cancer or cervical dysplasia, which method comprises determining the genetic status of at least one miRNA in the sample using a system comprising a plurality of probes, wherein at least about 50% of the probes are capable of detecting an miRNA having a nucleotide sequence that is set forth in SEQ ID NO:1-20 or their corresponding homologues, wherein a characteristic change in the genetic status of the miRNA indicates a high/low rate of survival for the individual. In some embodiments, the method further comprises determining a proper course of treatment for the individual.

Further provided herein is a method of classifying cervical intraepithelial and/or cervical patients based, for example, on expression levels of miRNAs or their corresponding homologues using a system comprising a plurality of probes, wherein at least about 50% of the probes are capable of detecting an miRNA having a nucleotide sequence that is set forth in SEQ ID NO:1-20 or their corresponding homologues.

Still further provided herein is a method for determining the level of differentiation of cervical dysplasia and/or cervical cancer in an individual, comprising determining the level of an miRNA using a system comprising a plurality of probes, wherein at least about 50% of the probes are capable of detecting an miRNA having a nucleotide sequence that is set forth in SEQ ID NO:1-20 or their corresponding homologues, wherein the expression level of the miRNA is used as a basis for determining the level of differentiation of cervical dysplasia and/or cervical cancer in the individual.

In another aspect, the present invention provides a method for diagnosing colorectal cancer, tongue squamous cell carcinoma, esophageal squamous cell carcinoma and pancreatic ductal adenocarcinoma in an individual, which method comprises determining a characteristic change in the level of miR-133b expression in a sample from the individual using the method for testing a sample for colorectal cancer, tongue squamous cell carcinoma, esophageal squamous cell carcinoma and pancreatic ductal adenocarcinoma, which method comprises: a) determining the level of miR-133b expression in the sample; b) comparing the level of miRNA expression with a reference level, and c) classifying the sample as cancerous if the sample exhibits a characteristic change in the level of miR-133b expression.

Further provided herein is a method for diagnosing colorectal cancer, tongue squamous cell carcinoma, esophageal squamous cell carcinoma and pancreatic ductal adenocarcinoma in an individual, which method comprises determining the genetic status of miR-133b in a sample from the individual using the method for testing a sample for colorectal cancer, tongue squamous cell carcinoma, esophageal squamous cell carcinoma and pancreatic ductal adenocarcinoma, which method comprises determining the genetic status of miR-133b, wherein a characteristic change in the genetic status of this miR-133b indicates the sample as cancerous.

In yet another aspect, provided in the present invention is a pharmaceutical composition for treating an individual with cervical cancer or cervical dysplasia, comprising an agent that decreases the level of at least one miRNA having a nucleotide sequence that is set forth in SEQ ID NO:1-13 or their corresponding homologues, and a pharmaceutically acceptable carrier. In one embodiment, the pharmaceutical composition further comprises an agent that increases the level of at least one miRNA having a nucleotide sequence that is set forth in SEQ ID NO:14-20 or their corresponding homologues.

Also provided herein is a pharmaceutical composition for treating an individual with cervical cancer or cervical dysplasia, comprising an agent that increases the level of at least one miRNA having a nucleotide sequence that is set forth in SEQ ID NO:14-20 or their corresponding homologues, and a pharmaceutically acceptable carrier.

Further provided herein is a method of treatment for an individual with cervical cancer or cervical dysplasia using the pharmaceutical composition comprising an agent that decreases the level of at least one miRNA having a nucleotide sequence that is set forth in SEQ ID NO:1-13 or their corresponding homologues, and a pharmaceutically acceptable carrier.

Still further provided herein is a method of treatment for an individual with cervical cancer or cervical dysplasia using a pharmaceutical composition comprising an agent that increases the level of at least one miRNA having a nucleotide sequence that is set forth in SEQ ID NO:14-20 or their corresponding homologues, and a pharmaceutically acceptable carrier.

In a further aspect, provided in the present invention is an oligonucleotide primer for amplifying an RNA sequence, which oligonucleotide probe comprises a nucleotide sequence that: a) hybridizes, under high stringency, with a nucleotide sequence, or a complementary strand thereof, that is set forth in Tables; or b) has at least 90% identity to a nucleotide sequence, or a complementary strand thereof, that is set forth in Tables. In one embodiment, the primer comprises a nucleotide sequence, or a complementary strand thereof, that is set forth in Tables. In another embodiment, the primer comprises DNA, RNA, PNA or a derivative thereof. In yet another embodiment, the primer is labeled. In a further embodiment, the label is selected from the group consisting of a chemical, an enzymatic, an immunogenic, a radioactive, a fluorescent, a luminescent and a FRET label.

The present invention also provides kits for methods described herein.

DETAILED DESCRIPTION OF THE INVENTION

Figure 1:
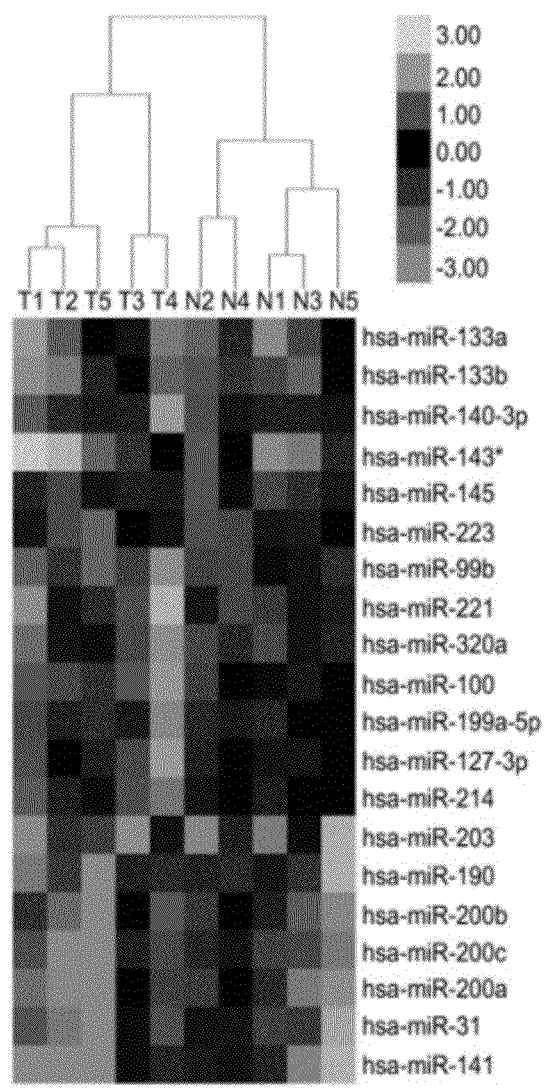
FIG. 1 provides hierarchical clustering of the miRNA expression levels analyzed by Significance Analysis of Microarrays (SAMs). There were 20 miRNAs differentially expressed in cervical cancer tissues (T1-T5) and normal cervical tissues (N1-N5), and profiles of the 20 miRNAs from 5 paired cervical tissue samples were clustered. Samples are shown in columns, miRNAs are shown in rows.

The present invention is based, in part, on the studies on miRNA expression profiling using a paired set of six normal cervical tissues, ten primary cervical cancer tissues and eight invasive cancer tissues. Specifically, using DNA oligonucleotide microarrays, the expression level of miRNAs of cancer samples with corresponding normal samples were compared. Twenty miRNAs that were either overexpressed or underexpressed in the cancer samples as compared to the corresponding normal samples were identified. Certain miRNAs whose expression levels were altered in different disease states were also identified. The expression level of hsa-miR-133b using quantitative reverse transcriptase polymerase chain reaction (RT-PCR) and in situ hybridization in cervical dysplasia and cervical cancer tissues was verified. Over-expression of hsa-miR-133b in cervical cancer promoted the formation and transformation of cancer.

Accordingly, in one aspect, the present invention provides systems for determining the expression level of miRNAs or the genetic status of miRNA genes. Also provided here in are oligonucleotide primers for amplification of miRNAs.

In another aspect, the present invention provides methods for classifying and determining prognosis for survival of cancer patients, particularly cervical dysplasia and/or cervical cancer patients, based on the expression levels of certain miRNAs or the genetic status of miRNA genes.

In a further aspect, the present invention provides pharmaceutical compositions and methods of treatment comprising an agent that alters the expression level of miRNAs.

Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a", "an", and "the" can mean singular or plural (i.e., can mean one or more) unless indicated otherwise.

An "individual" as used herein refers to a vertebrate, preferably a mammal, more preferably a human. Mammals include, but are not limited to, farm animals, sport animals, pets, primates, mice and rats. In some embodiments, the individual is human. In some embodiments, the individual is an animal model for the study of cervical cancer. It is understood that, when the individual is not human, the miRNA would refer to the corresponding homologs or orthologs of the human miRNA identified herein.

A "cervical tissue sample" described herein refers to a tissue sample from the cervices. In some embodiments, the tissue sample is a fresh sample. In some embodiments, the tissue sample is a frozen sample. In some embodiments, the tissue sample is preserved. In some embodiments, the tissue sample is formalin preserved. In some embodiments, the tissue sample is paraffin embedded. As described below, and depending on the particular method, the tissue can be used whole or subject to various methods known in the art to disassociate the sample into small pieces, cell aggregates or individual cells.

Cervical cancer includes, but is not limited to, cervical squamous cell cancer or cervical adenocarcinoma.

As used herein, the term "homologue" is used to refer to a nucleic acid which differs from a naturally occurring nucleic acid (i.e., the "prototype" or "wild-type" nucleic acid) by minor modifications to the naturally occurring nucleic acid, but which maintains the basic nucleotide structure of the naturally occurring form. Such changes include, but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5× Denhardt's solution, 5× SSPE, 0.2% SDS at 42° C., followed by washing in 0.2× SSPE, 0.2% SDS, at 42° C. High stringency conditions can be provided, for example, by hybridization in 50% formamide, 5× Denhardt's solution, 5× SSPE, 0.2% SDS at 42° C., followed by washing in 0.1× SSPE, and 0.1% SDS at 65° C. Low stringency hybridization refers to conditions equivalent to hybridization in 10% formamide, 5× Denhardt's solution, 6× SSPE, 0.2% SDS at 22° C., followed by washing in 1× SSPE, 0.2% SDS, at 37° C. Denhardt's solution contains 1% Ficoll, 1% polyvinylpyrolidone, and 1% bovine serum albumin (BSA). 20× SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, $2^{nd}$ ed., Cold Spring Harbor Press, Plainview, N.Y. (1989); and Ausubel et al., Short Protocols in Molecular Biology, $4^{th}$ ed., John Wiley & Sons (1999).

As used herein, "genetic status" refers to the structure, copy number, and chromosomal location of an miRNA gene. A "characteristic change" in the genetic status of an miRNA gene can be reflected, for example, by deletion or amplification, a change in copy number, or a change in chromosomal location, etc.

As used herein, a "characteristic change" in the expression levels of miRNAs can simply be a substantial decrease or a substantial increase in the expression level of an miRNA in a sample as compared to a reference level. A characteristic change may also refer to substantial changes in the expression level of more than one miRNA. It may also refer to substantial increases in the expression levels of some miRNAs and substantial decreases in the expression levels of other miRNAs.

For methods described herein, a "reference level" is generally a level that is considered "normal" for the particular miRNA. In some embodiments, the reference level is based on the level of the miRNA in the non-cancerous cervical intraepithelial or cervical tissue from the same individual. In some embodiments, the reference level is based on the level of an individual not having cervical dysplasia or cervical cancer. In some embodiments, the reference level is based on an average of levels obtained from a population that is not having cervical dysplasia or cervical cancer. In some embodiments, the reference level is derived from a pool of samples including the sample being tested. The reference level can be predetermined or determined contemporaneously with the sample being tested.

A reference level may be the level of another miRNA, the level of another RNA, such as U6, or the level of another nucleic acid, such as DNA. The level of miRNA expression may be compared to the level of other nucleic acids in the same sample or in a reference sample. A reference sample may be a sample from the same tissue or a different tissue, and may be from the same individual or from a different individual.

As used herein, a "reference value" can be an absolute value, a relative value, a value that has an upper or lower limit, a range of values, an average value, a median value, a mean value, or a value as compared to a particular control or baseline value.

As used herein, a "substantial" change means a change that can be readily detected by the methods as described herein, or a change that is statistically significant. A "substantial increase" as used herein may refer to an increase in miRNA level by at least about 5%, including for example at least any of 6%, 7%, 8%, 9%, 10%, 15%, 20%, 30%, 40%, 50%, or more. Similarly, a "substantial decrease" as used herein may refer to a decrease in miRNA level by at least about 5%, including for example at least any of 6%, 7%, 8%, 9%, 10%, 15%, 20%, 30%, 40%, 50%, or more.

The oligonucleotides for systems described herein include, for example, DNA, RNA, PNA, LNA, combinations thereof, and/or modified forms thereof. They may also include a modified oligonucleotide backbone. In some embodiments, the oligonucleotide comprises at least about any of 9, 10, 12, 13, 14, 15, 16, 17, 18, 19, 20, or more continuous oligonucleotides complementary or identical to all or part of a miRNA described herein. A single oligonucleotide may comprise two or more such complementary sequences. In some embodiments, there is a reactive group (such as an amine) attached to the 5' or 3' end of the oligonucleotide for attaching the oligonucleotide to a substrate.

Other objects, advantages and features of the present invention will become apparent from the following specification taken in conjunction with the accompanying drawings.

Systems for Determining miRNA Expression Level and Genetic Status

The present invention provides various systems for detecting miRNA expression levels that undergo characteristic changes in cervical dysplasia or cervical cancer patients. Also provided are systems for determining genetic status of miRNAs. The systems can be used for various purposes, including for example diagnosing cervical dysplasia or cervical cancer, classifying cervical dysplasia or cervical cancer patients, and determining a prognosis for survival of cervical dysplasia or cervical cancer patients.

The miRNAs described herein are also useful for one or more of the following: classifying cervical dysplasia or cervical cancer patients, predicting risk of developing cervical dysplasia or cervical cancer, monitoring tumor progression in cervical dysplasia or cervical cancer patients, and monitoring treatment in cervical dysplasia or cervical cancer patients, based on the expression level of one or more miRNAs in a cervical intraepithelial or cervical tissue sample, or the genetic status of one or more miRNAs in a cervical intraepithelial or cervical tissue sample of the individual.

The systems described herein comprise probes for detecting miRNAs and/or determining genetic status of miRNAs. While the discussion below focuses on systems that are capable of detecting miRNA expression levels, it is readily understood by a person of ordinary skill in the art that certain aspects of the description is equally applicable to systems comprising probes that are capable of determining gene deletion, amplification, and/or change in gene copy number of miRNA genes (collectively referred to as genetic status of the miRNA genes).

For example, in some embodiments, there is provided a system comprising a plurality of probes, wherein the probes are capable of detecting different miRNAs in a sample, and wherein at least about 15% (including for example at least about any of 20%, 30%, 40%, 50%, 60%, 70%, 80%, 90%, or 95%) of the probes are capable of detecting an miRNA shown in Table 1 or their corresponding homologues. In some embodiments, the system comprises (including for example consisting essentially of or consisting of) at least about any of 2, 5, 10, 20, 30, 40, or 50 probes, wherein each of the probes is capable of detecting an miRNA shown in Table 1 or their corresponding homologues.

TABLE 1

List of miRNAs with an Altered Level of Expression in Cervical Dysplasia and/or Cervical Cancer Patient Samples

| SEQ ID No: | miRNA | Expression Level | Chromosomal Location | Sequence |
|---|---|---|---|---|
| 1 | hsa-miR-133a | High | Ch 18: 19405659-19405746[-] Ch 20: 61162119-61162220[+] | 5'-tttggtcccttcaaccagctg-3' |
| 2 | hsa-miR-133b | High | Ch 6: 52013721-52013839[+] | 5'-tttggtcccttcaaccagcta-3' |
| 3 | hsa-miR-140-3p | High | Ch 16: 69966984-69967083[+] | 5'-uaccacaggguagaaccacgg-3' |
| 4 | hsa-miR-143* | High | Ch 5: 148808481-148808586[+] | 5'-ggugcagugcugcaucucuggu-3' |
| 5 | hsa-miR-145 | High | Ch 5: 148810209 148810296[+] | 5'-guccaguuucccaggaaucccu-3' |
| 6 | hsa-miR-223 | High | Ch X: 65238712 65238821[+] | 5'-ugucaguuugucaaauacccca-3' |
| 7 | hsa-miR-99b | High | Ch 19: 52195865-52195934[+] | 5'-cacccguagaaccgaccuugcg-3' |
| 8 | hsa-miR-221 | High | Ch X: 45605585-45605694[-] | 5'-agcuacauugucugcuggguuuc-3' |
| 9 | hsa-miR-320a | High | Ch 8: 22102475-22102556[-] | 5'-aaaagcgggguugagagggcga-3' |
| 10 | hsa-miR-100 | High | Ch 11: 122022937-122023016[-] | 5'-aacccguagauccgaacuugug-3' |
| 11 | hsa-miR-199a-5p | High | Ch 19: 10928102-10928172[-] Ch 1: 172113675-172113784[-] | 5'-cccaguguucagacuaccuguuc-3' |
| 12 | hsa-miR-127-3p | High | Ch 14: 101349316-101349412[+] | 5'-ucggauccgucugagcuuggcu-3' |

TABLE 1-continued

List of miRNAs with an Altered Level of Expression in Cervical Dysplasia and/or Cervical Cancer Patient Samples

| SEQ ID No: | miRNA | Expression Level | Chromosomal Location | Sequence |
|---|---|---|---|---|
| 13 | hsa-miR-214 | High | Ch 1: 172107938-172108047[-] | 5'-acagcaggcacagacaggcagu-3' |
| 14 | hsa-miR-203 | Low | Ch 14: 104583742-104583851[+] | 5'-gugaaauguuuaggaccacuag-3' |
| 15 | hsa-miR-190 | Low | Ch 15: 63116156-63116240[+] | 5'-ugauauguuugauauauuaggu -3' |
| 16 | hsa-miR-200b | Low | Ch 1: 1102484-1102578[+] | 5'-uaauacugccugguaaugauga -3' |
| 17 | hsa-miR-200c | Low | Ch 12: 7072862-7072929[+] | 5'-uaauacugccgguaaugaugga -3' |
| 18 | hsa-miR-200a | Low | Ch 1: 1103243-1103332[+] | 5'-uaacacugucugguaacgaugu-3' |
| 19 | hsa-miR-31 | Low | Ch 9: 21512114-21512184[-] | 5'-aggcaagaugcuggcauagcu-3' |
| 20 | hsa-miR-141 | Low | Ch 12: 7073260-7073354[+] | 5'-uaacacugucugguaaagaugg-3' |

The systems described herein may comprise two or more probes that detect the same miRNA. For example, in some embodiments where the system is a microarray, the probes may be present in multiple (such as any of 2, 3, 4, 5, 6, 7, or more) copies on the microarray. In some embodiments, the system comprises different probes that detect the same miRNA. For example, these probes may bind to different (overlapping or nonoverlapping) regions of the miRNA.

Any probes that are capable of determining the levels of miRNA can be used. In some embodiments, the probe may be an oligonucleotide. It is understood that, for detection of miRNAs, certain sequence variations are acceptable. Thus, the sequence of the oligonucleotides (or their complementary sequences) may be slightly different from those of the miRNAs described herein. Such sequence variations are understood by those of ordinary skill in the art to be variations in the sequence that do not significantly affect the ability of the oligonucleotide to determine miRNA levels. For example, homologs and variants of these oligonucleotide molecules possess a relatively high degree of sequence identity when aligned using standard methods. Oligonucleotide sequences encompassed by the present invention have at least 40%, including for example at least about any of 50%, 60%, 70%, 80%, 90%, 95%, or more sequence identity to the sequence of the miRNAs described herein. In some embodiments, the oligonucleotide comprises a portion for detecting the miR-NAs and another portion. Such other portion may be used, for example, for attaching the oligonucleotides to a substrate. In some embodiments, the other portion comprises a non-specific sequence (such as polyT) for increasing the distance between the complementary sequence portion and the surface of the substrate.

The oligonucleotides for the systems described herein include, for example, DNA, RNA, PNA, LNA, combinations thereof, and/or modified forms thereof. They may also include a modified oligonucleotide backbone. In some embodiments, the oligonucleotide comprises at least about any of 9, 10, 12, 13, 14, 15, 16, 17, 18, 19, 20, or more continuous oligonucleotides complementary or identical to all or part of an miRNA described herein. A single oligonucleotide may comprise two or more such complementary sequences. In some embodiments, there may be a reactive group (such as an amine) attached to the 5' or 3' end of the oligonucleotide for attaching the oligonuceotide to a substrate.

In some embodiments, the system is a microarray of probes. "Microarray" and "array," as used interchangeably herein, comprise a surface with an array, preferably an ordered array, of putative binding (e.g., by hybridization) sites for a biochemical sample (target) which often have undetermined characteristics. In some embodiments, a microarray refers to an assembly of distinct oligonucleotide probes immobilized at defined positions on a substrate.

For example, in some embodiments, there is provided a microarray comprising a plurality of probes, wherein each of the probes is capable of detecting a different miRNA in a sample, and wherein at least about 15% (including for example at least about any of 20%, 30%, 40%, 50%, 60%, 70%, 80%, 90%, or 95%) of the probes are capable of detecting an miRNA shown in Table 1 or their corresponding homologues.

In some embodiments, microarrays for determining the genetic status of miRNA genes corresponding to miRNAs disclosed herein are provided. Microarrays for determining genetic status are known in the art. For example, the system can comprise sequence-tagged molecular inversion probes for determining the genetic status.

Arrays may be formed on substrates fabricated with materials such as paper, glass, plastic (e.g., polypropylene, nylon, polystyrene), polyacrylamide, nitrocellulose, silicon, optical fiber or any other suitable solid or semisolid support, and configured in a planar (e.g., glass plates, silicon chips) or three dimensional (e.g., pins, fibers, beads, particles, microtiter wells, capillaries) configuration.

In some embodiments, the probes are oligonucleotides. Oligonucleotides forming the array may be attached to the substrate by any number of ways including, but not limiting to, (i) in situ synthesis (e.g., high-density oligonucleotide arrays) using photolithographic techniques; (ii) spotting/printing at medium to low density on glass, nylon or nitrocellulose; (iii) masking; and (iv) dot-blotting on a nylon or nitrocellulose hybridization membrane. Oligonucleotides may also be non-covalently immobilized on the substrate by hybridization to anchors, by means of magnetic beads, or in a fluid phase such as in microtiter wells or capillaries.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which may be coated with an aldehyde or another reactive group which can form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995), 93:10614-10619). Arrays can also be printed by robotics onto glass, nylon (Ramsay, G., Nature Biotechnol. (1998), 16:40-44), polypropylene (Matson, et al., Anal Biochem. (1995), 224(1):110-6), and silicone slides (Marshall and Hodgson, Nature Biotechnol. (1998), 16:27-31). Other approaches to array assembly include fine micropipetting within electric fields (Marshall, and Hodgson, Nature Biotechnol. (1998), 16:27-31), and spotting the polynucleotides directly onto positively coated plates. Methods such as those using amino propyl silicon surface chemistry are also known in the art, as disclosed at www.cmt.corning.com and http://cmgm.stanford.edu/pbrown/.

One method for making microarrays is by making high-density nucleotide arrays. Techniques are known for rapid deposition of polynucleotides (Blanchard, et al., Biosensors & Bioelectronics, 11:687-690). Other methods for making microarrays, e.g., by masking (Maskos and Southern, Nucleic. Acids. Res. (1992), 20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

MiRNAs for Diagnosis of Cervical Dysplasia or Cervical Cancer

The present invention identifies 20 miRNAs whose levels correlate with cervical dysplasia or cervical cancer. These miRNAs are shown in Table 1. Table 1 provides the name, sequence, and chromosomal location of the miRNAs. Information about miRNAs can be generally found at http://miRNA.sanger.ac.uk/ (Griffths-Jones, et al., Nucleic Acids Research, 2006, Vol. 34, Database issue). Methods of diagnosing cervical dysplasia or cervical cancer can be based on the levels or genetic status of any of the miRNAs shown in Table 1. Systems described herein can be used for determining the levels of one of more miRNAs shown in Table 1 and diagnosing cervical dysplasia or cervical cancer based on the levels of one or more miRNAs shown in Table 1.

Although acceptable levels of sensitivity and specificity with a single miRNA can be achieved for practice of the methods described herein, the effectiveness (e.g., sensitivity and/or specificity) of the methods described herein are generally enhanced when at least two miRNAs are utilized. For example, in some embodiments, at least 1, 2, 3, 4, 5, 6, 7, 8, 9, 10, 12, 15, 18, 20 miRNAs shown in Table 1 are utilized.

In some embodiments, the levels or genetic status of at least two (such as at least any of 2, 3, 5, 10 or more) miRNA of SEQ ID NO:1-13 are determined In some embodiments, the levels or genetic status of at least two (such as at least any of 2, 5, 7, or more) miRNAs of SEQ ID NO:14-20 are determined In some embodiments, the levels or genetic status of at least one of the miRNAs selected from the miRNAs of SEQ ID NO:1-13 and at least one of the miRNAs selected from the miRNAs of SEQ ID NO:14-20 are determined. In some embodiments, the levels or genetic status of at least two (such as at least any of 2, 3, 5, 10, or more) of the miRNAs selected from the miRNAs of SEQ ID NO:1-13 and the levels of at least two (such as at least any of 2,5,7, or more) miRNAs of SEQ ID NO:14-20 are determined. In some embodiments, the levels or genetic status of all miRNAs shown in Table 1 are determined.

In some embodiments, the levels of the corresponding homologues of the miRNA described herein are determined. The "corresponding homologues" of miRNA described herein refers to miRNAs having at least about 50% sequence identity (including for example at least about any of 60%, 70%, 80%, 90%, 95%, 98%, or 99%) sequence identity to the corresponding miRNA described herein. For example, the corresponding homologue of a miRNA of SEQ ID NO:1 has at least about 50% sequence identity (including for example at least about any of 60%, 70%, 80%, 90%, 95%, 98%, or 99%) sequence identity to SEQ ID NO:1.

An miRNA sequence that has at least about, for example, 95% identical to a reference sequence (such as SEQ ID NO:1) is intended that the miRNA sequence is identical to the reference sequence except that the miRNA sequence may include up to five point alterations per each 100 nucleotide of the reference sequence. These up to five point alterations may be deletions, substitutions, additions, and may occur anywhere in the sequence, interspersed either individually among nucleotides in the reference sequence or in one or more continuous groups within the reference sequence.

For the diagnosis of colorectal cancer, tongue squamous cell carcinoma, esophageal squamous cell carcinoma and pancreatic ductal adenocarcinoma, the expression level or genetic status of miR-133b is determined.

Methods for Diagnosis of Cancer, Particularly Cervical Dysplasia and Cervical Cancer The present invention in one aspect provides a method of diagnosing cervical dysplasia and cervical cancer in an individual, comprising: a) determining the level of at least one miRNA (such as at least one miRNA shown in Table 1 or their corresponding homologues) in a cervical intraepithelial or cervical tissue sample of the individual, wherein the tissue is suspected of being cancerous, and b) comparing the level of the miRNA with a reference level, wherein a characteristic change in the level of the miRNA is indicative of cervical dysplasia or cervical cancer. In some embodiments, the method further comprises the step of providing a cervical tissue sample from the individual. In some embodiments, the method further comprises isolating miRNAs from the tissue sample.

In some embodiments, there is provided a method of providing information for diagnosis of cervical dysplasia and cervical cancer in an individual comprising: a) determining the level of at least one miRNA shown in Table 1 or their corresponding homologues in a cervical tissue sample of the individual, wherein the tissue is suspected of being cancerous, and b) providing information about the level of the miRNA for diagnosis of cervical dysplasia or cervical cancer, wherein the level of the miRNA is used as basis for diagnosing cervical dysplasia or cervical cancer, and wherein a characteristic change in the level of the at least one miRNA is indicative of cervical dysplasia or cervical cancer.

In some embodiments, the level of at least one (such as at least any of 2, 3, 5, 10, 13) of the miRNAs of SEQ ID NO:1-13 are determined, wherein a substantial increase in the levels of at least one of the measured miRNAs is indicative of cervical dysplasia or cervical cancer. In some embodiments, the levels of at least one (such as at least any of 2, 5, 7) of the miRNAs of SEQ ID NO:14-20 are determined, wherein a substantial decrease in the levels of at least one of the measured miRNAs is indicative of cervical dysplasia or cervical cancer. In some embodiments, the levels of at least one (such as at least any of 2, 3, 5, 10, 13) of the miRNAs of SEQ ID NO:1-13 and at least one (such as at least any of 2, 5, 7) of the miRNAs of SEQ ID NO:14-20 are determined, wherein a substantial increase in the levels of at least one of the miRNA from Nos. 1-13 of Table 1 and a substantial decrease in the levels of at least one of the miRNAs from Nos. 14-20 are indicative of cervical dysplasia or cervical cancer.

In some embodiments, the levels of all miRNAs shown in Table 1 are determined, wherein a substantial increase in the levels of at least one of the miRNA of SEQ ID NO:1-13 and a substantial decrease in the levels of at least one of the miRNAs of SEQ ID NO:14-20 are indicative of cervical dysplasia or cervical cancer. In some embodiments, a substantial increase in the levels of at least two of the miRNAs of SEQ ID NO:1-13 and a substantial decrease in the levels of at least two of the miRNAs of SEQ ID NO:14-20 are indicative of cervical dysplasia or cervical cancer. In some embodiments, a substantial increase in the levels of miRNAs of SEQ ID NOs. 1-13 and a substantial decrease in the levels of the miRNAs of SEQ ID NOs. 14-20 are indicative of cervical dysplasia or cervical cancer.

Levels of miRNA expression in the tissue sample may also reflect changes of the genetic status of the miRNAs. Genetic status can be reflected, for example, by deletion or amplification of the miRNA gene or by a change in gene copy number of the miRNA gene.

Accordingly, in some embodiments, there is provided a method of diagnosing cervical dysplasia and/or cervical cancer in an individual, comprising analyzing the genetic status of at least one miRNA gene (such as at least one miRNA gene corresponding to an miRNA shown in Table 1) in a cervical intraepithelial or cervical tissue sample suspected of being cancerous in an individual, wherein a characteristic change in the genetic status relative to the corresponding miRNA gene in a control sample is indicative of cervical dysplasia or cervical cancer. In some embodiments, the change of the genetic status is determined based on a deletion or amplification of the miRNA gene. In some embodiments, the change of the genetic status is determined based on the change in gene copy number of the miRNA gene.

In some embodiments, there is provided a method of diagnosing cervical dysplasia and/or cervical cancer in an individual, comprising analyzing at least one miRNA gene corresponding to at least one miRNA shown in Table 1 in a cervical intraepithelial or cervical tissue sample suspected of being cancerous from the individual for deletion or amplification, wherein a deletion or amplification of the miRNA gene relative to the corresponding miRNA gene in a control sample is indicative of cervical dysplasia or cervical cancer. For example, in some embodiments, the method comprises analyzing at least one miRNA gene corresponding to at least one miRNA of SEQ ID NO:1-13 for amplification, wherein an amplification of the miRNA gene relative to the corresponding miRNA gene in a control sample is indicative of cervical dysplasia or cervical cancer. In some embodiments, the method comprises analyzing at least one miRNA gene corresponding to at least one miRNA of SEQ ID NO:14-20 for deletion, wherein a deletion of the miRNA gene relative to the corresponding miRNA gene in a control sample is indicative of cervical dysplasia or cervical cancer. In some embodiments, the method further comprises the step of providing a cervical intraepithelial or cervical tissue sample suspected of being cancerous from the individual. In some embodiments, the method further comprises the step of isolating DNA from the cervical intraepithelial or cervical tissue sample.

In some embodiments, there is provided a method of diagnosing cervical dysplasia and/or cervical cancer in an individual, comprising determining the gene copy number of at least one miRNA gene corresponding to at least one of the miRNAs shown in Table 1 or their corresponding homologues in a cervical intraepithelial or cervical tissue sample suspected of being cancerous from the individual, wherein a copy number other than two for miRNA genes located on a somatic chromosome or a sex chromosome is indicative of cervical dysplasia or cervical cancer. For example, in some embodiments, the method comprises determining the gene copy number of at least one miRNA gene corresponding to at least one of the miRNAs of SEQ ID NO:1-13 in a sample from the individual, wherein a copy number more than two for miRNA genes located on a somatic chromosome or a sex chromosome is indicative of cervical dysplasia or cervical cancer. In some embodiments, the method comprises determining the gene copy number of at least one miRNA gene corresponding to at least one of the miRNAs of SEQ ID NO:14-20 in a sample from the individual, wherein a copy number less than two for miRNA genes located on a somatic chromosome or a sex chromosome is indicative of cervical dysplasia or cervical cancer. In some embodiments, the method further comprises the step of providing a cervical intraepithelial or cervical tissue sample suspected of being cancerous from the individual. In some embodiments, the method further comprises the step of isolating DNA from the cervical intraepithelial or cervical tissue sample.

In some embodiments, the method of diagnosing cervical dysplasia or cervical cancer is based on expression levels of the miRNAs.

In another aspect, the present invention provides a method of diagnosing colorectal cancer, tongue squamous cell carcinoma, esophageal squamous cell carcinoma and pancreatic ductal adenocarcinoma, comprising: a) determining the level of miR-133b in a tissue sample of the individual, wherein the tissue is suspected of being cancerous, and b) comparing the level of the miR-133b with a reference level, wherein a characteristic change in the level of the miR-133b is indicative of colorectal cancer, tongue squamous cell carcinoma, esophageal squamous cell carcinoma or pancreatic ductal adenocarcinoma.

Accordingly, in some embodiments, there is provided a method of diagnosing colorectal cancer, tongue squamous cell carcinoma, esophageal squamous cell carcinoma and pancreatic ductal adenocarcinoma in an individual, comprising analyzing the genetic status of miR-133b gene in a tissue sample suspected of being cancerous in an individual, wherein a characteristic change in the genetic status of miR-133b gene relative to the corresponding miR-133b gene in a control sample is indicative of colorectal cancer, tongue squamous cell carcinoma, esophageal squamous cell carcinoma or pancreatic ductal adenocarcinoma. In some embodiments, the change of the genetic status is determined based on a deletion or amplification of the miR-133b gene. In some embodiments, the change of the genetic status is determined based on the change in gene copy number of the miR-133b gene.

As used interchangeably herein, the terms "expression level" and "level" refer to the amount or rate of accumulation of an miRNA molecule or its precursor. The terms can be used to refer to the absolute amount of an miRNA in a sample (as represented by the intensity of a hybridization signal, for example), or the ratio of the amount of the miRNA to that of a control (as represented by the ratio of the hybridization signal of the sample to that of a control, for example). The control can be a different miRNA from the same sample whose level does not alter in a cervical dysplasia or cervical cancer tissue sample, or can be the same miRNA from a different sample (such as a noncancerous tissue sample from the same individual or a tissue sample from another individual not having cervical dysplasia or cervical cancer).

The "precursor" of an miRNA molecule or "miRNA precursor" refers to the unprocessed miRNA gene transcript, and typically comprises an RNA transcript of about 70 nucleotides in length. The miRNA precursors are typically processed by digestion with an RNAase (such as Dicer, Argonaut, or RNAase III) into an active miRNA molecule, which are typically 19-25 nucleotide long.

A "level of miRNA in a cervical intraepithelial or cervical tissue sample" refers to the miRNA level in the tissue sample. While in most cases the level of the miRNA in a cervical intraepithelial or cervical tissue sample is determined based directly on measuring the miRNA level in a cervical intraepithelial or cervical tissue sample, it is contemplated that the miRNA level in a cervical intraepithelial or cervical tissue sample can also be reflected by (and thus based on) the level of miRNA in a lymph node sample (such as the proximal lymph nodes or lymph fluid), serum, blood, or other proximal biological fluid materials such as sputum. In some embodiments, the miRNA level is determined based on the level of the miRNA in a lymph node sample (such as a lymph node section or needle aspirate). In some embodiments, the miRNA level is determined based on the level of the miRNA in the blood or serum. In some embodiments, the miRNA level is determined based on the level of the miRNA in a cervical intraepithelial or cervical tissue swab. In some embodiments, the miRNA level is determined based on the level of the miRNA from a sample that is obtained by endoscopic ultrasound-guided sampling procedures (for example by RT-PCR analysis). Endoscopic ultrasound-guided fine-needle aspiration (FNA) is a minimally invasive technique for the non-operative sampling of mediastinal lymph nodes, which allows more detailed molecular marker analysis. Determination of miRNA levels in samples other than cervical dysplasia or cervical cancer tissues can be used along or in conjunction with each other. For example, the level of the miRNA can first be determined from the serum, then a follow-up analysis of miRNA in regional lymph nodes can be conducted. Such multi-step analysis could provide additional information and increase confidentiality of the diagnosis.

miRNA levels can be determined in various stages. For example, the miRNA level can be determined immediately prior to surgery, during surgery, after the surgery, prior to tumor treatment, during tumor treatment, or after tumor treatment.

Methods of determining levels of miRNAs are known in the art. For example, miRNA levels can be determined by Northern blot, in situ hybridization, RT-PCR, and microarrays (Einat, Methods Mol. Biol. (2006), 342:139-157; Thompson, et al., Genes Dev. (2006), 20:2202-2207).

According to one exemplary method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., Northern blotting techniques. The RNA is then immobilized on the filters by heating. Detection and quantification of specific RNA is accomplished using appropriately labeled DNA or RNA probes complementary to the RNA in question. Autoradiographic detection of probe hybridization to miRNA can be performed by exposing hybridized filters to photographic film. Densitometric scanning of the photographic film exposed by the hybridized filters provides an accurate measurement of RNA transcript level. Alternatively, RNA transcript level can be quantified by computerized imaging of the hybridization blot, for example with a phosphoimager.

In addition to Northern and other RNA blotting hybridization techniques, the levels of RNA transcripts can be carried out according to the technique of in situ hybridization. This technique involves depositing whole cells or tissues onto a microscopic cover slip and probing the nucleic acid content of the cell or tissue with a solution containing radioactive or otherwise labeled probes (such as cRNA probes).

The levels of the miRNAs can also be determined by RT-PCR. The levels of the miRNAs can be quantified in comparison with an internal standard, for example, levels of mRNA from a "housekeeping" gene present in the same sample. A suitable "housekeeping" gene for use as an internal standard include myosin or glyceraldehydes-3-phosphate dehydrogenase (G3PDH) or human U6. The methods for quantitative RT-PCR and variations thereof are well known to those of ordinary skill in the art. In certain instances, real-time quantitative PCR (qRT-PCR) analysis of miRNAs may be more sensitive than classical tissue sectioning and staining for detecting miRNAs in some early-stage cancer. The qRT-PCR for miRNA level determination provided herein may provide a sensitive and specific tool for the diagnosis, classification, and prognosis of cervical dysplasia or cervical cancer. The present invention in one aspect provides methods of determining the miRNA level in a sample of an individual (such as an individual having a disease, for example cancer) by RT-PCR. In some embodiments, the level of the miRNA is determined by qRT-PCR.

In some embodiments, the levels of miRNAs are determined by using a microarray, such as microarrays described herein.

Nucleic acid probes for one or more methods described above can be produced recombinantly or chemically synthesized using methods well known in the art. Additionally, hybridization probes can be labeled with a variety of detectable labels including, for example, radioisotopes, fluorescent tags, reporter enzymes, biotin and other ligands. Such detectable labels can additionally be coupled with, for example, calorimetric or photometric indicator substance for spectrophotometric detection. Methods for labeling and detecting such probes are known in the art.

Nucleic acid probes useful for detecting miRNAs in a sample can be hybridized under various stringency conditions readily determined by one skilled in the art. Depending on the particular assay, one skilled in the art can readily vary the stringency conditions to optimize detection of a particular miRNA in a particular sample.

In some embodiments, levels of the miRNA may be obtained from an individual at more than one time point. Such "serial" sampling is well suited for the aspects of the present invention relating to monitoring progression of cervical dysplasia or cervical cancer in an individual having cervical dysplasia or cervical cancer. Serial sampling can be performed on any desired timeline, such as semi-annually, annually, biennially, or less frequently. The comparison between the measured levels and the reference level may be carried out each time a new sample is measured, or the data relating to levels may be held for less frequent analysis.

A comparison to a reference value may be performed for at least any of 1, 2, 3, 4, 5, 6, 7, 8, 9, 10, 15, 18, 20, or 20 miRNAs shown in Table 1 or their corresponding homologues. The process of comparing the levels of an miRNA with a reference level can be carried out in any convenient manner appropriate to the type of measured values for the miRNAs at issue. For example, when hybridization signals of the miRNAs used as a measure of miRNA levels, the levels may be compared qualitatively by visually comparing the intensities of the hybridization signals. For quantitative measures, the comparison can be made by inspecting the numerical data, inspecting representations of the data (e.g., inspecting graphical representations such as bar or line graphs). The process of comparing may be manual (such as visual inspection by the practitioner of the methods) or it may be automated.

In some embodiments, the comparison is performed by determining the magnitude of the difference between the measured and reference levels (e.g., comparing the "fold" or percentage difference between the measured and reference levels). As used herein, the phrase "fold difference" refers to a numerical representation of the magnitude difference between a measured value and a reference value for an miRNA.

Table 1 provides a summary of changes of the listed miRNAs in one exemplary method. A characteristic change of the levels of the miRNAs is used as a basis for diagnosing cervical dysplasia or cervical cancer. For example, in some embodiments when the level of at least one of the miRNAs of SEQ ID NO:1-13 is determined, a substantial increase in the levels of at least one of the measured miRNAs is indicative of cervical dysplasia or cervical cancer. In some embodiments when at least one of the miRNAs of SEQ ID NO:14-20 are determined, a substantial decrease in the levels of at least one of the measured miRNAs is indicative of cervical dysplasia or cervical cancer. In some embodiments when at least one of the miRNAs of SEQ ID NO:1-13 and at least one of the miRNAs of SEQ ID NO:14-20 are determined, a substantial increase in the levels of at least one of the miRNA from SEQ ID NO:1-13 of Table 1 and a substantial decrease in the levels of at least one of the miRNAs from SEQ ID NO:14-20 is indicative of cervical dysplasia or cervical cancer.

In some embodiments, the levels of all miRNAs shown in Table 1 are determined, and a substantial increase in the levels of at least one of the miRNA of SEQ ID NO:1-13 and a substantial decrease in the levels of at least one of the miRNAs of SEQ ID NO:14-20 are indicative of cervical dysplasia or cervical cancer. In some embodiments, a substantial increase in the levels of at least two of the miRNAs of SEQ ID NO:1-13 and a substantial decrease in the levels of at least two of the miRNAs of SEQ ID NO:14-20 are indicative of cervical dysplasia or cervical cancer.

In those embodiments when more than one miRNAs are used but the levels of the miRNAs do not unanimously suggest or indicate a diagnosis of cervical dysplasia or cervical cancer, the "majority" suggestion or indication may be considered the result of the assay. For example, when the method utilizes five miRNAs, 3 of which suggest/indicate cervical dysplasia or cervical cancer, the result may be considered as suggesting or indicating a diagnosis of cervical dysplasia or cervical cancer for the individual. However in some embodiments, a diagnosis of cervical dysplasia or cervical cancer requires a characteristic change of at least one, or more, specific miRNAs. For example, in cases when one of the miRNAs is hsa-miR-133b, a substantial increased level of hsa-miR-133b in some embodiments may be prerequisite for a diagnosis of cervical dysplasia or cervical cancer.

Methods of Diagnosis Based on Genetic Status of miRNAs

Also provided herein are methods of diagnosing cervical dysplasia or cervical cancer based on the genetic status of at least one miRNAs shown in Table 1 or their corresponding homologues in the sample of an individual.

In some embodiments, the genetic status is evaluated by analyzing at least one miRNA gene in the sample for deletion or amplification, wherein the detection of a deletion or amplification in the miRNA gene relative to the miRNA in a control sample is indicative of the presence of cervical dysplasia or cervical cancer in the individual.

A deletion or amplification in an miRNA gene can be detected by determining the structure or sequence of genes in cells from a cervical intraepithelial or cervical tissue sample from an individual suspected of having cervical dysplasia or cervical cancer, and comparing this with the structure or sequence of these genes in cells from a control sample. Any techniques suitable for detecting alteration in the structure or sequence of genes can be used in the practice of the present method. For example, the presence of miRNA gene deletions and amplifications can be detected by Southern Blot hybridization of the genomic DNA from a subject, using nucleic acid probes specific for miRNA sequences. Sequence analyses and single strand conformational polymorphism can also be used.

Deletions or amplifications of an miRNA gene can also be detected by amplifying a fragment of these genes by PCR, and analyzing the amplified fragment by sequencing or electrophoresis to determine if the sequence or length of the amplified fragment from the individual's DNA sample is different from that of a control DNA sample. Deletion of an miRNA gene can also be identified by detecting deletions of chromosomal markers that are closely linked to the miRNA gene.

The status of an miRNA gene in cells of an individual can also be evaluated by measuring the copy number of at least one miRNA gene in the sample, wherein a gene copy number other than two for miRNA genes on somatic chromosomes and sex chromosomes is indicative of the presence of cervical dysplasia or cervical cancer in the individual.

Any techniques suitable for detecting gene copy number can be used in the practice of the present method, including the Southern blot and PCR amplification techniques. An alternative method of determining the miRNA gene copy number in a cervical intraepithelial or cervical tissue sample relies on the fact that many miRNAs or gene clusters are closely linked to chromosomal markers or other genes. The loss of a copy of an miRNA gene in an individual who is heterozygous at a marker or gene closely linked to the miRNA gene can be inferred from the loss of heterozygosity in the closely linked marker or gene. Methods for determining loss of heterozygosity of chromosomal markers are within the skill in the art.

A "control sample" can be a tissue sample from an individual not having cervical dysplasia or cervical cancer. Alternatively, the control sample can be a collection of tissue samples from a population of individuals.

Genetic status can be determined for at least any of 1, 2, 3, 4, 5, 6, 7, 8, 9, 10, 15, 18, or 20 miRNAs shown in Table 1 or their corresponding homologues. In those embodiments when the genetic status of more than one miRNAs are used but do not unanimously suggest or indicate a diagnosis of cervical dysplasia or cervical cancer, the "majority" suggestion or indication may be considered the result of the assay. For example, when the method utilizes five miRNAs, 3 of which suggest/indicate cervical dysplasia or cervical cancer, the result may be considered as suggesting or indicating a diagnosis of cervical dysplasia or cervical cancer for the individual. However in some embodiments, a diagnosis of cervical dysplasia or cervical cancer requires a characteristic change of at least one, or more, specific miRNA genes.

Various techniques can be used to determine the genetic status of the miRNA genes. These include, for example, allele-specific primer extension on microarrays, PCR/LDR universal arrays, microsphere-based single base chain extension, sequence-tagged molecular inversion probes, and combinatorial sequence-by-hybridization.

Also provided herein are methods of diagnosing colorectal cancer, tongue squamous cell carcinoma, esophageal squamous cell carcinoma and pancreatic ductal adenocarcinoma based on the genetic status of miR-133b or its corresponding homologues in the sample of an individual. In some embodiments, the genetic status is evaluated by analyzing the miR-133b gene in the sample for deletion or amplification, wherein the detection of a deletion or amplification of the miR-133b gene relative to the miR-133b gene in a control sample is indicative of the presence of colorectal cancer, tongue squamous cell carcinoma, esophageal squamous cell carcinoma and pancreatic ductal adenocarcinoma in the individual.

Methods for Prognosis for Survival of Cervical Dysplasia or Cervical Cancer Patients The present invention in another aspect provides methods of prognosticating cervical dysplasia or cervical cancer patients, including for example methods of determining a prognosis for survival of an individual having cervical dysplasia or cervical cancer. The prognostic methods of the present invention are useful for determining a proper course of treatment for an individual having cervical dysplasia or cervical cancer. For example, a determination of the likelihood of survival can assist in determining whether a more conservative or more radical approach to therapy should be taken, or whether treatment modalities should be combined. In addition, such prognosis can help determine whether agents for improving survival (such as agents described herein) are necessary and/or effective.

In some embodiments, there is provided a method for determining a prognosis for survival for an individual having cervical dysplasia or cervical cancer, comprising: (a) determining the level of at least one miRNA in a cervical dysplasia or cervical cancer tissue sample from the individual, and (b) comparing the level of the miRNA in said sample to a threshold level, wherein the level of the miRNA as compared to a threshold level correlates or reversely correlates with the survival of the individual. As used herein, "correlate" means that a low level of the miRNA as compared to the threshold level is indicative of a low survival of the individual having cervical dysplasia or cervical cancer, and vise versa. As used herein, "revise correlate" means that a high level of the miRNA as compared to the threshold level is indicative of a high survival rate, and vise versa.

In some embodiments, the gene corresponding to the miRNA is located to any of Chromosome 6, Chromosome 18, and Chromosome 20. In some embodiments, at least one miRNA is hsa-miR-133b.

In some embodiments, there is provided a method of determining a prognosis for survival for an individual having cervical dysplasia or cervical cancer, comprising: (a) determining the level of at least one miRNA in a cervical dysplasia or cervical cancer tissue sample from the individual, and (b) comparing the level of the miRNA in said sample to a threshold level, wherein the level of the miRNA as compared to the threshold level reversely correlates with the survival of said individual, and wherein at least one miRNA is hsa-miR-133b or its corresponding homologues. In some embodiments, at least one miRNA is hsa-miR-133b.

Levels of the miRNAs described herein may also reflect changes in the genetic status of the miRNAs (such as miRNAs described herein). In some embodiments, there is provided a method of determining a prognosis for survival for an individual having cervical dysplasia or cervical cancer, comprising analyzing the genetic status of at least one miRNA genes (such as a miRNA gene corresponding to hsa-miR-133b or its corresponding homologues), wherein a change in genetic status as compared to a that of a control sample indicates a high or low survival of the individual. For example, in some embodiments, there is provided a method of prognosis for survival for an individual having cervical dysplasia or cervical cancer, comprising analyzing at least one miRNA gene for amplification, wherein an amplification of the miRNA gene relative to the corresponding miRNA gene in a control sample correlates with a low survival rate of the individual, and wherein at least one miRNA is hsa-miR-133b or its corresponding homologues. In some embodiments, there is provided a method of prognosis for survival of an individual having cervical dysplasia or cervical cancer, comprising determining the gene copy number of at least one miRNA gene, wherein a copy number of more than two indicates a low survival rate of the individual, and wherein at least one miRNA is hsa-miR-133b or its corresponding homologues.

Use of Probes for Detecting the Level of miRNA

Also provided herein are uses of probes that are capable of detecting the levels of the miRNAs (or the genetic status of the corresponding miRNA gene) or systems comprising one or more probes for determining a prognosis for survival. For example, in some embodiments, there is provided a use of one or more probes (or system comprising one or more probes) for determining prognosis for survival of an individual having cervical dysplasia or cervical cancer, wherein the probe is capable of detecting an miRNA in the sample, and wherein the level of the miRNA as compared to the threshold level correlates or reversely correlates with the survival of said individual. In some embodiments, there is provided a use of one or more probes for determining prognosis of survival of an individual having cervical dysplasia or cervical cancer, wherein the level of the miRNA as compared to the threshold level reversely correlates with the survival of said individual, and wherein at least one miRNA is hsa-miR-133b or its corresponding homologues.

In some embodiments, there is provided a use of one or more probes for the manufacture of an agent (or system) for determining a prognosis of survival of an individual having cervical dysplasia or cervical cancer, wherein the probe is capable of detecting an miRNA in the sample, and wherein the level of the miRNA as compared to the threshold level correlates or reversely correlates with the survival of said individual. In some embodiments, there is provided a use of one or more probe for the manufacture of an agent (or system)

for determining prognosis of survival of an individual having cervical dysplasia or cervical cancer, wherein the level of the miRNA as compared to the threshold level reversely correlates with the survival of said individual, and wherein at least one miRNA is hsa-miR-133b or its corresponding homologues.

The survival described herein can be disease free survival or overall survival. As used herein, the term "disease-free survival" refers to the lack of tumor recurrence and/or spread and the fate of an individual after diagnosis, for example, an individual who is alive without tumor recurrence. The phase "overall survival" refers to the fate of the individual after diagnosis, regardless of whether the individual has a recurrence of the tumor.

Threshold Level

Certain methods and uses described herein involve determining a prognosis for survival based on miRNA levels relative to a threshold level.

The threshold level can be determined by a plurality of methods, provided that the resulting threshold level accurately provides a level of miRNA above which exist a first group of patients having a different survival rate than that of a second group of patients having an miRNA level below the threshold level.

The threshold level can be determined by, for example, the miRNA level of a non-cancerous cervical dysplasia or cervical cancer tissue sample. The threshold level can also be determined by analyzing the levels of an miRNA in a population of individuals having cervical dysplasia or cervical cancer. This can be accomplished, for example, by histogram analysis, in which an entire cohort of tested individuals are graphically presented, wherein a first axis represents the level of the miRNA, and a second axis represents the survival rate of the individual. Two or more separate groups of individuals can be determined by identification of subset populations of the cohort which have the same or similar levels of the miRNA. Determination of the threshold level can then be made based on an miRNA level which best distinguish these separate groups. For example, in some embodiments, the threshold level can be based on the mean value of the average miRNA level of a group with high survival rate and the average miRNA level of a group with low survival rate. A threshold level also can represent the levels of two or more miRNAs. Two or more miRNAs can be represented, for example, by a ratio of values for levels of each miRNA.

The threshold level can be a single number that is equally applicable to every individual having cervical dysplasia or cervical cancer, or vary according to a specific subpopulation of individuals. For example, older women might have a different threshold level than younger women. Furthermore, a threshold level can be a level determined for each individual. For example, the threshold level may be a certain ratio of an miRNA in the cervical dysplasia or cervical cancer tissue relative to the miRNA level in a non-cancerous tissue within the same individual.

Verification that the threshold level distinguishes the likelihood of survival in cervical dysplasia or cervical cancer patients expressing below threshold level versus patients expressing above threshold level can be carried out using single variable or multi-variable analysis. These methods determine the likelihood of a correlation between one or more variables and a given outcome. In the specific case, the methods will determine the likelihood of a correlation between an miRNA level and disease free or overall survival of cancer patient. Any one of a plurality of methods well known to those of ordinary skill in the art for carrying out these analyses can be used. Examples of single variable analysis are the Kaplan-Meir method or the Cox proportional-hazards regression model.

Population-based determination of threshold levels, for example, by histogram analysis can be carried out using a cohort of patients sufficient in size in order to determine two or more separate groups of patients having different miRNA levels. Typically, such a cohort comprises at least 25 patients, including for example at least about any of 50, 75, 100, 125, 150, or 200 patients. Similarly, verification of determined threshold levels can also comprises at least 25 patients, including for example at least about any of 50, 75, 100, 125, 150, or 200 patients.

Furthermore, while a single threshold level can separate two groups of patients, several threshold values might exist which separate a plurality of populations. For example, two threshold values can separate a first group of patients with high levels of miRNA from a second group of patients with intermediate levels of miRNA, and from a third group of patients with low levels of the miRNA. The number of different threshold levels can be sufficient to proscribe a curve, such as a continuous line, which describes the likelihood of disease-free or overall survival in a patient as a function of the miRNA level in that patient. Such a curve will constitute a "continuous" miRNA level, where the likelihood of disease free or overall survival in a patient is proportional to the miRNA level in that patient. Two or more miRNA levels can be represented by such a curve.

In some embodiments, the miRNA (such as miRNAs described herein) can be combined with each other in the methods of the present invention for determining prognosis for survival of a cancer patient. The use of a combination of two or more miRNAs can provide increased prognostic significance or confidence in a prognostic determination.

The level of an miRNA can also be used in conjunction with another variable found to be statistically significant as indicators of the likelihood of disease-free or overall survival for cervical dysplasia or cervical cancer patient, such as pathological indicators (for example, age, tumor size, tumor histology, clinical stage, family history and the like). For example, clinical stage of the cancer is a statistically significant indicator of disease-free or overall survival, wherein the threshold level can vary according to the clinical stage of the cancer. Hence, the threshold level of an miRNA can vary as a function of another statistically significant indicator of disease-free or overall survival for cervical dysplasia or cervical cancer.

In one exemplary method, Kaplan-Meier analysis is used to determine the correlation between survival rate and the miRNA level.

In some embodiments, the method comprises: (a) determining a level of at least one miRNA in a cervical dysplasia or cervical cancer tissue from the individual, (b) classifying the individual as belonging to either a first or second group of individuals having cervical dysplasia or cervical cancer, wherein the first group of individuals having a low levels of the miRNA is classified as having an increased likelihood of survival compared to the second group of individuals having high level of the miRNA, wherein at least one miRNA is hsa-miR-133b.

After the levels of one or more miRNAs in patient sample have been determined and compared to a threshold level, the patient is then classified into a group having a certain likelihood of disease free or overall survival. Then the likelihood of disease-free or overall survival for the patient is assessed based on the likelihood of disease-free or overall survival for patients in that group.

For example, a sample can be determined to have low levels of miRNA. This patient would then be classified into a group of patients having low levels of miRNA. Because it has been established that there is an increased likelihood of disease-free or overall survival for the group of patients expressing low levels of miRNA, the specific cancer patient would be considered to have an increased likelihood of disease free or overall survival.

The methods described herein may further comprise a step of determining the proper course of treatment for the individual. One of ordinary skill in the art would appreciate that the prognostic indicators of survival for cancer patients suffering from an early stage of cancer may be different from those for cancer patients suffering from a later stage of cancer. For example, prognosis for stage I cancer patient may be oriented toward the likelihood of continued growth and/or metastasis of the cancer, whereas prognosis for stage IV cancer patient may be oriented toward the likely effectiveness of therapeutic methods for treating the cancer. The determination of proper course of treatment will therefore take these variables into account.

Pharmaceutical Compositions and Methods of Treatment for Treating an Individual with Cervical Cancer or Cervical Dysplasia In some embodiments, there is provided a pharmaceutical composition comprising an agent that decreases the level of an miRNA and a pharmaceutically acceptable carrier, wherein at least one miRNA is hsa-miR-133b, hsa-miR-140-3p, hsa-miR-143*. In some embodiments, at least one miRNA is hsa-miR-133b. In some embodiments, at least one miRNA is hsa-miR-140-3p. In some embodiments, at least one miRNA is hsa-miR-143*. In some embodiments, the agent is a double-stranded RNA (such as short or small-interfering RNA or "siRNA"), an antisense nucleic acid, or an enzymatic RNA molecule such as ribozyme. Methods and compositions for improving survival are further described below in more detail.

Also provided are methods of improving survival of a cervical dysplasia or cervical cancer patient using agents that decreases the levels of certain miRNAs, such as hsa-miR-133b, hsa-miR-100, hsa-miR-140-3p, hsa-miR-143*.

Any agents that can decrease the level of miRNAs can be used in methods of the present invention. Suitable agents for inhibiting miRNA gene expression include, but are not limited to, double-stranded RNA (such as short or small-interfering RNA or "siRNA"), antisense nucleic acids, enzymatic RNA molecules such as ribozyme, small molecule compounds, and proteins. These agents can be used alone or in combination with other agents (such as other agents described herein). The agents can decrease the miRNA levels directly (e.g., by inhibiting the miRNA expression or function) or indirectly (e.g., by affecting the genetic status of the corresponding miRNA gene).

For example, expression of a given miRNA gene can be inhibited by inducing RNA interference of the miRNA gene with an isolated double-stranded RNA ("dsRNA") molecule which has at least 70%, including for example at least any of 75%, 80%, 85%, 90%, 95%, 98%, 99%, or 100%, sequence homology with at least a portion of the miRNA gene product. In some embodiments, the dsRNA molecule is a short or small interfering RNA ("siRNA").

siRNA useful in the present methods may comprise short double-stranded RNA of about 10-30 nucleotides, including for example about any of 12-28, 14-26, 16-24, or 18-22 nucleotides. The siRNA comprises a sense RNA strand and a complementary antisense RNA strand annealed together by standard Watson-Crick base-pairing interactions. The sense strand comprises a nucleic acid sequence which is substantially identical to a nucleic acid sequence contained within the target miRNA. The sense and antisense strands of the siRNA can comprises two complementary, single-stranded RNA molecules, or can comprise a single molecule in which two complementary portions are base-paired and are covalently linked by a single-stranded "hairpin" area.

The siRNA can differ from naturally-occurring RNA by the addition, deletion, substitution and/or alteration of one or more nucleotides. Such alteration can include addition of non-nucleotide material, such as to the end(s) of the siRNA or one or two internal nucleotides of the siRNA, or modifications that make the siRNA resistant to nuclease digestion, or the substitution of one or more nucleotides in the siRNA with deoxynucleotides. In some embodiments, one or both strands of the siRNA also comprise a 3' overhang. The siRNA can be produced chemically or biologically, or can be expressed from a recombinant plasmid or viral vector, as described further below.

Expression of a given miRNA can also be inhibited by an antisense nucleic acid. As used herein, an "antisense nucleic acid" refers to a nucleic acid molecule that binds to target RNA by means of RNA-RNA or RNA-DNA interactions, which alters the activity of the target RNA. Antisense nucleic acids suitable for use in the present methods are single-stranded nucleic acids (e.g., RNA, DNA, RNA-DNA chimeras, PNA, and LNA) that generally comprise a nucleic acid sequence complementary to a contiguous nucleic acid sequence in a miRNA. In some embodiments, the antisense nucleic acid comprises a nucleic acid sequence that is at least about any of 70%, 75%, 80%, 85%, 90%, 95%, or 100% complementary to a contiguous nucleic acid sequence in an miRNA. In some embodiments, the antisense nucleic acid has about 10-30 nucleotides, including for example, about any of 12-28, 14-26, 16-24, or 18-22 nucleotides.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector, as further described below.

Expression of a given miRNA gene can also be inhibited by an enzymatic nucleic acid. As used herein, an "enzymatic nucleic acid" refers to a nucleic acid comprising a substrate binding region that is complementary to a contiguous nucleic acid sequence of an miRNA, and which is able to specifically cleave the miRNA. In some embodiments, the enzymatic nucleic acid binding region is 50-100% complementary, including for example 75-100% complementary, or 95-100% complementary to a contiguous nucleic acid sequence in a miRNA. The enzymatic nucleic acid can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as further described below.

A variety of methods are known in the art for introducing a nucleic acid molecule into a cell, including a cancer cell. Such methods include microinjection, electroporation, lipofection, calcium-phosphate mediated transfection, DEAE-Dextran-mediated transfection, microparticle bombardment, delivery by a colloidal dispersion system (such as macromolecular complexes, beads, oil-in-water emulsions, micelles, mixed micelles, and liposomes), and conjugation to an antibody, gramicidin S, artificial viral envelopes or other intracellular carriers such as TAT.

A nucleic acid agent can also be delivered into a mammalian cell in vitro or in vivo using suitable vectors known in the art. Suitable vectors for delivering a nucleic acid to a mammalian cell, include viral vectors and non-viral vectors such as plasmid vector. Such vectors are useful for providing therapeutic amounts of an agent such as antisense RNA or siRNA.

Viral based systems provide the advantage of being able to introduce relatively high levels of the heterologous nucleic acid into a variety of cells. Suitable viral vectors for introducing a nucleic acid include, for example, Herpes simplex virus vectors, vaccinia virus vectors, cytomegalovirus vectors, Moloney murine leukemia virus vectors, adenovirus vectors, adeno-associated virus vectors, retrovirus vectors, and lentivirus vectors. The tropism of the vital vectors can also be modified by pseudotyping the vectors with envelope proteins or surface antigens from other viruses. For example, an AAV vector can be pseudotyped with surface proteins from vesicular stomatitis virus (VSV) rabies, Ebola, Mokola, and the like.

Any of a variety of inducible promoters or enhancers can also be included in a nucleic acid or vector of the present invention to allow control of expression of the antisense RNAs or siRNAs, by added stimuli or molecules. Such inducible systems include, for example, tetracycline inducible systems, metalothionein promoter induced by heavy metals, insect steroid hormone responsive to ecdysone or related steroids such as muristerone, mouse mammary tumor virus (MMTV) induced by steroids such as glucocorticoid and estrogen, and heat short promoters inducible by temperature changes.

An agent is in an effective amount if the amount of the agent is enough to decrease the level of miRNA. In some embodiments, the agent decreases the level of the miRNA by about any of 10%, 20%, 30%, 40%, or 50% of the difference between the miRNA level and threshold level. Exemplary amounts for the agents (such as nucleic acid agents) include, but are not limited to, 0.1-3000 mg/kg body weight, 10-2000 mg/kg body weight, 50-1000 mg/kg body weight, 100-500 mg/kg body weight. In some embodiments, the amount of the agent (such as any of the nucleic acid agents) is about 10-500 mg/gram tumor mass, such as any of 20-300 mg/gram tumor mass, 50-200 mg/gram tumor mass, and 100-150 mg/gram tumor mass.

One of ordinary skill in the art can readily determine an appropriate dosage regimen for the administration of the agents to an individual. Exemplary dosing frequency for the agents includes, but is not limited to, at least about any of once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day(s). In some embodiments, the interval between each administration is constant. For example, the administration can be carried out daily, every two days, every three days, every four days, every five days, or weekly. In some embodiments, the administration can be carried out twice daily, three times daily, or more frequent.

The administration of the agent can be extended over an extended period of time, such as from about a month up to about three years. For example, the dosing regime can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The composition described herein can be administered to an individual via any route in the art, including, but not limited to, intravenous, intraperitoneal, intraocular, intra-arterial, intrapulmonary, oral, intravesicular, intramuscular, intra-tracheal, subcutaneous, intraocular, intrathecal, transdermal, transpleural, intraarterial, topical, inhalational (e.g., as mists of sprays), transmucosal (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the composition is administered systemically. In some embodiments, the composition is administered locally.

Also provided herein are pharmaceutical compositions comprising an agent that decreases the level of an miRNA and a pharmaceutically acceptable carrier. In some embodiments, the pharmaceutical composition comprises an agent that decreases the level of a miRNA selected from the group consisting of hsa-miR-133b or its corresponding homologues. In some embodiments, at least one miRNA is hsa-miR-133b. In some embodiments, the agent is a siRNA. In some embodiments, the agent is an antisense RNA. In some embodiments, the agent is a ribozyme.

In some embodiments, the pharmaceutical compositions are sterile. In some embodiments, the pharmaceutical compositions are pyrogene-free.

Suitable pharmaceutically acceptable carriers include, for example, water, buffered water, normal saline, 0.4% saline, 0.3% glycine, and hyaluronic acid. The pharmaceutical compositions may also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide) or calcium or sodium salts (for example, calcium chloride, calcium ascorbate, calcium gluconate or calcium lactate). Pharmaceutical compositions of the present invention can be packaged for use in liquid form, or can be lyophilized.

For solid pharmaceutical compositions of the present invention, conventional nontoxic solid pharmaceutically acceptable carriers can be used, for example, pharmaceutical grades of mannitol, lactose, starch, magnesium stearate, sodium saccharin, talcum, cellulose, glucose, sucrose, magnesium carbonate, and the like.

The present invention also provides methods of improving survival of individuals having cervical dysplasia or cervical cancer. In some embodiments, there is provided a method of improving survival of an individual having cervical dysplasia or cervical cancer, comprising administering to the individual an effective amount of an agent that decreases the level of an miRNA, wherein the level of the miRNA as compared to the threshold level reversely correlates with the survival of said individual. In some embodiments, there is provided a use of an agent that decreases the level of an miRNA for the manufacture of a medicament for improving survival of an individual having cervical dysplasia or cervical cancer, wherein the level of the miRNA as compared to the threshold level reversely correlates with the survival of said individual.

In some embodiments, there is provided a method of improving survival of an individual having cervical dysplasia or cervical cancer, comprising administering to the individual an effective amount of an agent that decreases the level of an miRNA selected from the group consisting of hsa-miR-133b, hsa-miR-140-3p, and their corresponding homologues. In some embodiments, there is provided use of an agent for the manufacture of a medicament for improving survival of an individual having cervical dysplasia or cervical cancer, wherein the agent decreases the level of an miRNA selected from the group consisting of hsa-miR-133b, hsa-miR-140-3p, and their corresponding homologues.

The methods described herein may further comprises a step of determining for prognosis for survival of the individual (for example, by methods described herein) prior to the administration of the agents.

In some embodiments, the levels of more than one miRNAs are decreased. This can be achieved, for example, by use of an agent that decreases the levels of two or more miRNAs. Alternatively, two or more agents are used for decreasing the levels of two or more miRNAs. For example, in some embodiments, there is provided a method of improving survival of an individual having cervical dysplasia or cervical cancer, comprising administering to the individual an effective amount of one or more agents that decreases the levels of at least two miRNAs selected from the group consisting of hsa-miR-133b, hsa-miR-140-3p, hsa-miR-143* and their corresponding homologues. In some embodiments, there is provided use of one or more agents for the manufacture of a medicament for improving survival of an individual having cervical dysplasia or cervical cancer, wherein the agent decreases the levels of at least two miRNAs selected from the group consisting of hsa-miR-133b, hsa-miR-140-3p, hsa-miR-143* and their corresponding homologues. In some embodiments, there is provided a method of improving survival of an individual having cervical dysplasia or cervical cancer, comprising administering to the individual an effective amount of one or more agents that decreases the levels of hsa-miR-133b, hsa-miR-140-3p and hsa-miR-143*. In some embodiments, there is provided use of one or more agents for the manufacture of a medicament for improving survival of an individual having cervical dysplasia or cervical cancer, wherein the agent decreases the levels of hsa-miR-133b, hsa-miR-140-3p and hsa-miR-143*.

Oligonucleotide Primers for Amplification of miRNAs

In a further aspect, provided in the present invention is an oligonucleotide primer for amplifying an RNA sequence, which oligonucleotide probe comprises a nucleotide sequence that: a) hybridizes, under high stringency, with a nucleotide sequence, or a complementary strand thereof, that is set forth in Table 2; or b) has at least 90% identity to a nucleotide sequence, or a complementary strand thereof, that is set forth in Table 2.

The present primers can comprise any suitable types of nucleic acids, e.g., DNA, RNA, PNA or a derivative thereof. Preferably, the probes comprise a nucleotide sequence, or a complementary strand thereof, that is set forth in Table 2. Also preferably, the probes are labeled, e.g., a chemical, an enzymatic, an immunogenic, a radioactive, a fluorescent, a luminescent and a FRET label.

The oligonucleotide primers can be produced by any suitable method. For example, the primers can be chemically synthesized (See generally, Ausubel (Ed.) Current Protocols in Molecular Biology, 2.11. Synthesis and purification of oligonucleotides, John Wiley & Sons, Inc. (2000)), isolated from a natural source, produced by recombinant methods or a combination thereof. Synthetic oligonucleotides can also be prepared by using the triester method of Matteucci et al., *J. Am. Chem. Soc.*, 3:3185-3191 (1981). Alternatively, automated synthesis may be preferred, for example, on an Applied Biosynthesis DNA synthesizer using cyanoethyl phosphoramidite chemistry. Preferably, the primers are chemically synthesized.

Suitable bases for preparing the oligonucleotide primers of the present invention may be selected from naturally occurring nucleotide bases such as adenine, cytosine, guanine, uracil, and thymine. It may also be selected from nonnaturally occurring or "synthetic" nucleotide bases such as 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carboxymethylaminomethyl uridine, dihydrouridine, 2'-O-methylpseudouridine, beta-D-galactosylqueosine, 2'-Omethylguanosine, inosine, N6 -isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6 -methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6 -isopentenyladenosine, N-((9-.beta.-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl)carbamoyl)threonine, 2'-O-methyl-5-methyluridine, 2'-O-methyluridine, wybutosine, and 3-(3-amino-3-carboxypropyl)uridine.

Likewise, chemical analogs of oligonucleotides (e.g., oligonucleotides in which the phosphodiester bonds have been modified, e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide (Shaw et al., *Nucleic Acids Res.*, 19:747 (1991)). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides (Milligan et al., *J. Med. Chem.*, 36:1923 (1993)). Many different chemical strategies have been employed to replace the entire phosphodiester backbone with novel linkages. Backbone analogues include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) (MMI) or methyleneoxy (methylimino) (MOMI) linkages. Phosphorothioate and methylphosphonate-modified oligonucleotides are particularly preferred due to their availability through automated oligonucleotide synthesis. The oligonucleotide may be a "peptide nucleic acid" such as described by (Milligan et al., *J. Med. Chem.*, 36:1923 (1993)). The only requirement is that the oligonucleotide primer should possess a sequence at least a portion of which is capable of binding to a portion of a target RNA sequence.

Kits

The present invention also provides kits for various methods described herein.

For example, in some embodiments, there is provided a kit containing a system (such as microarrays) for determine miRNA levels as described herein. In some embodiments, the kit further comprises additional reagents for carrying out the assays. The kit may further comprise an instruction or user manual detailing preferred methods of performing the methods of the present invention, and/or a reference to a site on the Internet where such instructions may be obtained.

In some embodiments, there is provided a kit containing a system (such as microarray) described herein for diagnosing cervical dysplasia or cervical cancer. The kit may further comprise control sample(s) for determination of a reference level, and/or information about obtaining a reference level. In some embodiments, the kit may further comprise instructions on use of the kits for diagnosing cervical dysplasia or cervical cancer, as described herein.

In some embodiments, there is provided a kit containing a system (such as microarray) described herein for classifying individuals having cervical dysplasia or cervical cancer. The kit may further comprise control samples for classifying the individual and/or information about control samples, and in some embodiments, instructions on use of the kit for classifying individuals.

In some embodiments, there is provided a kit containing a system (such as microarray) described herein for diagnosing colorectal cancer, tongue squamous cell carcinoma, esophageal squamous cell carcinoma or pancreatic ductal adenocarcinoma. The kit may further comprise control sample(s) for determination of a reference level, and/or information about obtaining a reference level. In some embodiments, the kit may further comprise instructions on use of the kits for diagnosing colorectal cancer, tongue squamous cell carcinoma, esophageal squamous cell carcinoma or pancreatic ductal adenocarcinoma, as described herein.

In some embodiments, there is provided a kit containing a system (such as microarray) described herein for classifying individuals having colorectal cancer, tongue squamous cell carcinoma, esophageal squamous cell carcinoma or pancreatic ductal adenocarcinoma. The kit may further comprise control samples for classifying the individual and/or information about control samples, and in some embodiments, instructions on use of the kit for classifying individuals.

In some embodiments, there is provided a kit for determining a prognosis for survival of an individual having cervical dysplasia or cervical cancer. Such a kit may comprise, for example, probes that detect an miRNA. In some embodiments, the kit further comprises a control sample for the determination of a threshold level and/or information about obtaining a threshold level. In some embodiments, the kit may further comprise instruction on use of the kit to determine prognosis of survival of an individual. In some embodiments, the kit may further comprise agents that decrease the levels of miRNA or pharmaceutical compositions comprising such agents for improvement of survival.

The kits described herein may further comprise reagents, which include, but are not limited to, substrates, labels, primers, reagents for labeling miRNAs, reagents for isolating miRNA, negative or positive controls for hybridization and detection, tubes and/or other accessories, reagents for collecting tissue sample, buffers, hybridization chambers, cover slips, etc., and may also contain a software package, e.g., for analyzing miRNA levels and/or characteristic changes of miRNA levels using statistical methods as described herein, and optionally a password and/or account number for assessing the compiled database.

In some embodiments, there is provided a kit comprising a pharmaceutical composition comprising an agent that decreases the level of an miRNA and an instruction on use of the composition for improvement of survival in an individual having cervical dysplasia or cervical cancer. In some embodiments, the kit further comprises vectors or other agents for delivery of the composition. In some embodiments, the kit further comprises instructions on administration of the pharmaceutical composition.

EXAMPLES

The following examples are offered to illustrate but not to limit the present invention.

Example 1

Preparation of Samples and Analysis of miRNA Levels by Using miRNA Microarray

Patients and Samples

Five pairs of cervical cancer tissues and corresponding normal cervical tissues were used. These specimens were obtained from patients in The First Teaching Hospital of Xinjing Medical University from 2006 to 2008 with informed consent and agreement. All tissue samples were from untreated patients undergoing surgery, and they were formalin-fixed paraffin-embedded (FFPE) until the extraction of miRNA. The tumor cell concentrations were evaluated and tumor histology was confirmed by a pathologist. The study was approved by the medical-ethics committee of The First Teaching Hospital of Xinjing Medical University.

Fabrication of the miRNA Microarray

Altogether 509 mature miRNA sequences were assembled and integrated into our miRNA microarray design, which comprised 435 human (including a further 122 predicted miRNA sequences from published references (Xie et al., 2005), 196 rat and 261 mouse mature miRNAs from the miRNA Registry (http://microrna.sanger.ac.uk; accessed September 2005)). In addition, 8 short oligonucleotides were designed that possessed no homology to any known RNA sequence and we produced their corresponding synthetic miRNAs by in vitro transcription using Ambion's miRNA Probe Construction kit (Cat. No. 1550, Austin, Tex.). Various amounts of these synthetic miRNAs were added into the human miRNA samples prior to analysis as internal controls.

All of the miRNA probe sequences were designed to be fully complementary to their cognate full-length mature miRNA. To facilitate probe immobilization onto the aldehyde modified-surface of the glass slides (CapitalBio Corp.), the probe sequences were concatenated up to a length of 40 nt (3'-end miRNA probe plus 5'-end 19mer polyT) with C6 5'-amino-modifier. Oligonucleotide probes were synthesized at MWG Biotech. Company and dissolved in EasyArray™ spotting solution (CapitalBio Corp.) at a concentration of 40 μM. Each probe was printed in triplicate using a SmartArray™ microarrayer (CapitalBio Corp.).

Labeling of Target RNAs

Purification of total RNA from paraffin-embedded tissue sections was performed as described previously (Varnholt et al., 2008). Briefly, tissue sections (20-μm) were deparaffinized in xylene and washed with 100% ethanol. Then, samples were digested with proteinase K at 55° C. for 12 h. Total RNA was extracted by phenol/chloroform and subsequently precipitated by isopropanol. After suspension in water, the concentration of total RNA was determined using the NanoDrop ND-1000 spectrophotometer (Nano-Drop Technologies, Wilmington, Del.). The T4 RNA ligase labeling method was adopted according to Thomson's protocol (Thomson et al., 2004). In brief, 4 μg of low-molecular-weight RNA was labeled with 500 ng of 5'-phosphate-cytidyl-uridyl-cy3-3' (Dharmacon, Lafayette, Colo.) with 2 units T4 RNA ligase (New England Biolabs, Beijing, China). The labeling reaction was performed at 16° C. for 4 h. Labeled RNA was precipitated with 0.3 M sodium acetate and 2.5 volumes ethanol and after washing with ethanol and drying was resuspended in 15 μl of hybridization buffer containing 3×SSC, 0.2% SDS and 15% formamide.

Slide Hybridization

Hybridization was performed under LifterSlip™ (Erie, Portsmouth, N.H.) in a hybridization chamber which was placed in a three-phase-tiling agitator BioMixe™ (CapitalBio) to provide continuous mixing of the hybridization buffer that results in more uniform hybridization across the entire slide surface and prevents edge effects, the efficiency of which has been demonstrated with our genome-wide mRNA expression profiling. The hybridization was performed overnight in water-bath at 50° C. The array was then washed with two consecutive washing solutions of 0.2% SDS, 2×SSC at 50° C. for 5 min, and 0.2% SSC for 5 min at room temperature. Arrays were scanned with a confocal LuxScan™ scanner and the images obtained were then analyzed using LuxScan™ 3.0™ software (both from CapitalBio).

Computational Analysis

Average values of the replicate spots of each miRNA were background subtracted, normalized, and subjected to further analysis. Normalization was performed by using per chip median normalization method and the median array. Data were filtered to eliminate genes with expression signal lower than 500 in all samples. Differentially expressed miRNAs were identified by Significance Analysis of Microarrays (SAM) (available at www-stat.stanford.edu/~tibs/SAM/index.html). SAM calculates a score for each gene on the basis of the change in expression relative to the standard deviation of all measurements. Hierarchical clustering was performed with average linkage and Pearson correlation. Clustering results of differentially expressed miRNAs are shown in FIG. 1. Comparing with normal cervical tissues, the expression levels of 13 miRNA genes were up-regulated and the expression levels of 7 miRNA genes were down-regulated.

Example 2

Discrimination between hsa-miR-133a and hsa-miR-133b by RT-PCR

The results of Example 1 showed that the expression levels of hsa-miR-133a and hsa-miR-133b were up-regulated in cervical carcinomas. As shown in Table 1, mammalian hsa-miR-133 has two mature isoforms, hsa-miR-133a and hsa-miR-133b, which differ at a single 3'-terminal base, although the pre-miR-133a and -133b sequences are more different. Specific primers have been designed according to the pre-miR-133a and -133b sequences and used for discrimination of these two isoforms. The pre-miR-133a and -133b sequences can be downloaded from the following website: http://microrna.sanger.ac.uk/ (Griffiths-Jones, et al., Nucleic Acids Research (2006) Vol. 34, Database issue).

Primers used for the amplification of pre-hsa-miR-133a and pre-hsa-miR-133b are listed in Table 2. Total RNA from 6 normal cervical tissues and 6 cervical carcinomas were purified as described in Example 1. The reverse transcription (RT) reaction contains 10 ng/μl of total RNA, 25 nM of RT primer, 1× RT buffer, 0.25 mM of dNTP, 7.5 U of Thermo-Script™ reverse transcriptase and 0.25 U/ml of RNase inhibitor (Invitrogen, Carlsbad, Calif.). The reaction system (20 μl) was incubated at 60° C. for 30 min, 85° C. for 5 min and then held to 4° C.

Figure 2:
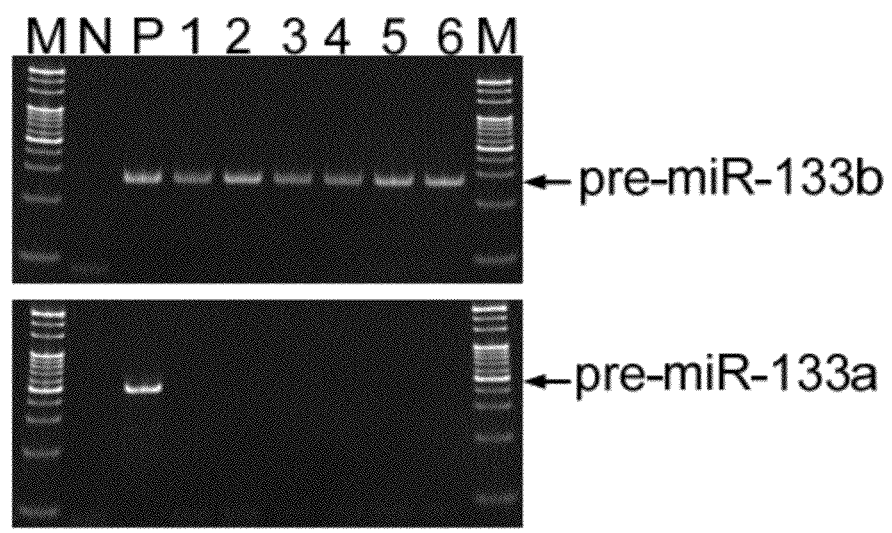
FIG. 2 provides the discrimination results of the two isoforms by pre-miRNA amplification. N: no template (negative control); P: pcDNA3.1-miR-133b or pcDNA3.1-miR-133a as the template (positive control); 1-6: cDNA from carcinoma samples as templates; M: 20 bp DNA Ladder Marker, from top to bottom: 500, 400, 300, 200, 180, 160, 140, 120, 100, 80, 60, 40, 20 bp.

Pre-miRNA amplification reaction (50 μl) contains 200 nM of dNTP, 1× PCR buffer, 15 nM of sense primer, 15 nM of antisense primer, 2 μl of RT product, 1.25 U of HotStar® Taq DNA polymerase (Qiagen). The PCR reaction is carried out as follows: 95° C., 10 min; 95° C., 15 sec, 70° C., 20 sec, 40 cycles. The amplicons are separated by 8% polyacrylamide gel electrophoresis (FIG. 2). Pre-miRNA amplification results showed that cervical carcinoma tissues express pre-hsa-miR-133b, while pre-hsa-miR-133a is hardly detectable. Thus, the up-regulation of hsa-miR-133 in cervical carcinomas is mainly contributed by hsa-miR-133b.

TABLE 2

Primers for the amplification of pre-miR-133a and pre-miR-133b

| RNA ID | Primer | Sequence |
| --- | --- | --- |
| Pre-hsa-miR-133a | Forward primer | 5' GCGGCGGTGCTTTGCTAGAGCTGGTAAAA 3' |
| | RT and reverse primer | 5' CGGCGGAGCTACAGCTGGTTGAAGGG 3' |
| Pre-hsa-miR-133b | Forward primer | 5' CGCGGCTGCTCTGGCTGGTCAAACG 3' |
| | RT and reverse primer | 5' CGGCGGTCAGGAAGACGGACTTGGTT 3' |

Example 3

Analysis of miRNA Levels by RT-PCR

Total cellular RNAs were prepared from FFPE tissues as described in Example 1. Reverse transcriptase reaction (10 μl) contained 10 ng of total RNA, 2 μl of RT primer (Exiqon, Vedbaek, Denmark), 1× RT buffer, 0.2 mM each of dNTPs, 0.5 μl of reverse transcriptase and 0.5 μl of RNase inhibitor. The reactions were incubated in an MJ Research PTC-225 Thermocycler for 30 min at 50° C., 5 min at 85° C. and then held at 4° C. All reverse transcriptase reactions, including no-template controls, were run in duplicate. The RT-PCR employed a mercury LNA™ microRNA PCR System kit (Exiqon) and a LightCycler (Roche Diagnostics, Mannheim, Germany) following the manufacturer's protocols. The PCR reaction (20 μl) included 4 μl of 10× diluted RT product, 10 μl of SYBR® Green master mix (Exiqon), 1 μl of LNA™ PCR primer and 1 μl of Universal PCR primer (Exiqon). The reactions were incubated at 95° C. for 10 min, followed by 60 cycles of 95° C. for 10 s, 60° C. for 20 s.

Figure 3:
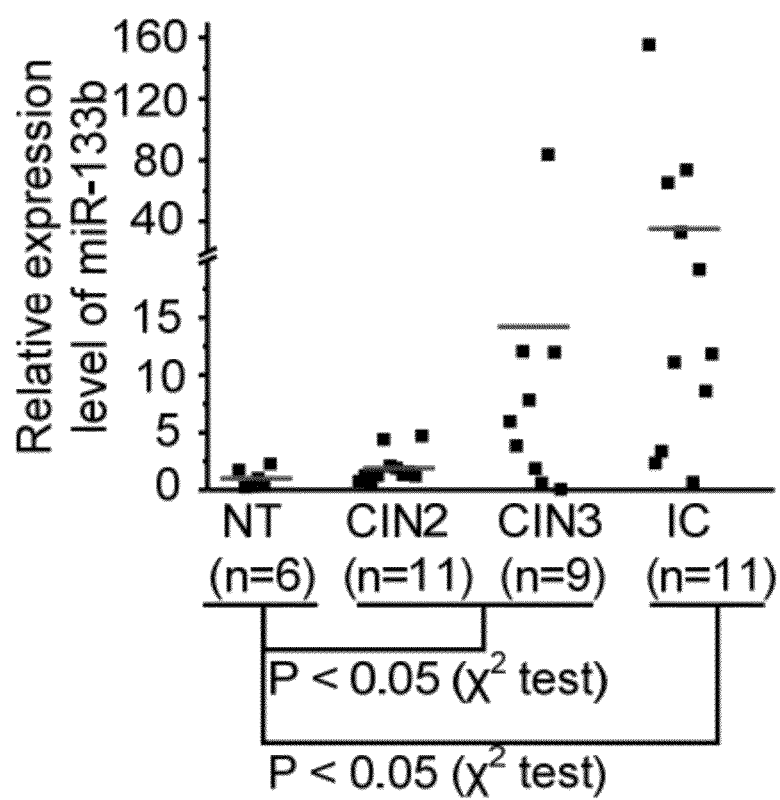
FIG. 3 provides the quantification results of the expression levels of hsa-miR-133b in different cervical tissues by using quantitative RT-PCR. Red lines indicate mean levels of hsa-miR-133b. NT: normal tissue; CIN 2: CIN grade 2; CIN 3: CIN grade 3; IC: invasive cancer.

All qRT-PCR reactions, including no-template controls were performed in duplicate. The relative expression ratios of miRNAs were determined with the crossing point (CP) as the cycle number. Gene Expression Assays for human U6 were used as the endogenous controls. The results were analyzed using LightCycler software version 3.5 (Roche Diagnostics). The real-time PCR amplification product was analyzed by melting curve analysis and agarose gel electrophoresis confirmation. The primer sequences are listed in Table 3. As shown in FIG. 3, the hsa-miR-133b levels continuously increased from normal tissues to CIN 2, to CIN 3 and to invasive carcinoma.

TABLE 3

Sequences of RT-PCR Primers

| RNA ID | Primer | Sequence |
|---|---|---|
| U6 | RT | AACGCTTCACGAATTTGCGT |
|  | Forward | CTCGCTTCGGCAGCACA |
|  | Reverse | AACGCTTCACGAATTTGCGT |
| hsa-miR-133b | RT, forward and reverse primers were purchased from Exiqon | |

Example 4

Figure 4:
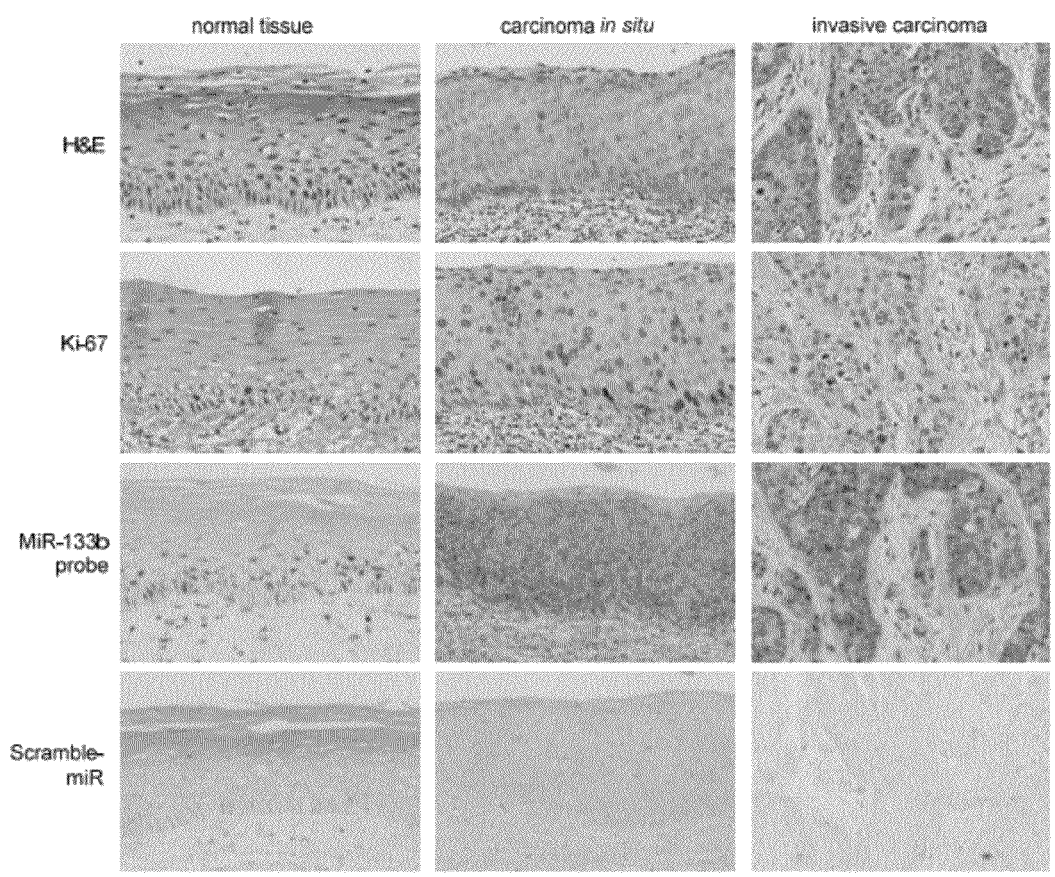
FIG. 4 shows results of in situ hybridization to verify the level of hsa-miR-133b expression in different cervical tissues. H&E: hematoxylin and eosin staining; Ki-67 IHC, immunohistochemistry with anti-Ki-67 antibody; MiR-133b or Scramble-miR ISH: in situ hybridization with MiRCURY LNA miR-133b detection probe or Scramble-miR (Exiqon, Vedbaek, Denmark); NT: normal tissue; CIN 3: CIN grade 3; IC: invasive cancer.

Confirmation of the Up-Regulation of hsa-miR-133b in Cervical Carcinoma Tissues by in situ Hybridization In situ hybridization experiments were performed according to the protocol provided by Exiqon (Vedbaek, Denmark) (http://www.exiqon.com/uploads/LNA_52-_FFPE_miR-NA_in_situ_protocol.pdf). Hybridization was carried out at 45° C. overnight with a miRCURY LNA™ miR-133b detection probe (50 nM) (Exiqon). The same reaction with Scramble-miR (Exiqon) was performed as negative control. As shown in FIG. 4, H&E staining and Ki-67 immunohistochemical staining showed normal cervical epithelium, CIN 3 and invasive cervical carcinoma. In situ hybridization results showed that only the basal cells in normal cervical epithelium express hsa-miR-133b, while all carcinoma cells in CIN 3 and invasive carcinoma highly express hsa-miR-133b.

Example 5

Xenograft Experiments by Using Severe Combined Immuno-Deficiency (SCID) Mouse Confirm that hsa-miR-133b Promotes Tumorigenesis of Cervical Carcinoma The hsa-miR-133b gene was amplified from human genomic DNA by using primers 5' CTGACAGGATCCG-TAAGAGGACATTCTGGACAAGGCAAGC 3' and 5' CGCACGAATTCATTCCTGGGAGCATAA-GAATATGGTGAAA 3'. The PCR product was digested by BamHI and EcoRI and then cloned into pcDNA3.1-neomycin vector (Invitrogen). Recombinant plasmid was sequence confirmed. The pcDNA3.1-hsa-miR-133b plasmid and empty vector (negative control) were separately transfected into CaSki cells (Cell Resource Center, Chinese Academy of Medical Sciences). G418 (800 μg/ml) was used for the selection of stable cell lines. Over-expression of hsa-miR-133b in stable cell lines was confirmed by real-time RT-PCR.

Figure 5:
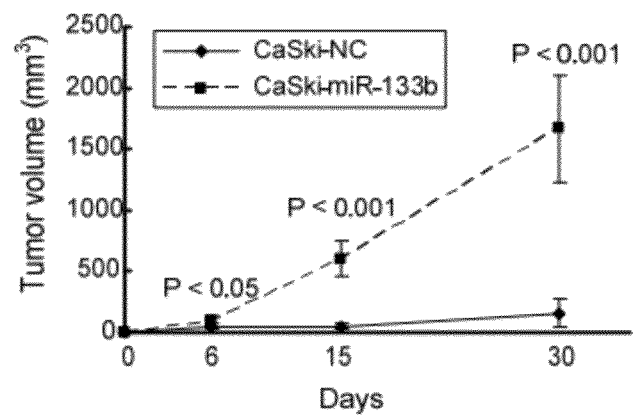
FIG. 5 shows the tumor growth curves in SCID mice. For each group, n=8. CaSki-NC represents CaSki stable cell lines constructed using empty vectors (pcDNA 3-neomycin) as negative control, whereas CaSki-miR-133b represents CaSki stable cell lines constructed using miR-133b-expressing plasmids (pcDNA3-miR-133b).

A total of 5×10$^6$ CaSki stable cells were injected s.c. into each 4-6-week-old female SCID mouse. Eight mice were used for each stable cell line. Tumor width and length were measured every 3 days, and tumor volumes were calculated. As shown in FIG. 5, the volumes of the tumors formed by hsa-miR-133b over-expressing cells were significantly larger than those of the tumors formed by control cells, indicating that hsa-miR-133b can promote tumorigenesis.

Example 6

Experimental Metastasis Results Show that hsa-miR-133b Promotes Metastasis

The hsa-miR-133b gene was subcloned into a new vector expressing puromycin resistant gene. The constructed plasmid expressing hsa-miR-133b in Example 5 and the empty vector pcDNA3.1-neomycin were digested by Bgl II and Pvu II enzymes and the small fragments were gel purified. The pSIREN-RetroQ vector (Clontech, Mountain View, Calif.) was first digested by EcoR I and filled in by using T4 DNA polymerase. Then, the plasmid was digested by Bgl II and the large fragment was gel purified. The purified small and large fragments were ligated by T4 DNA ligase and transfected into E. coli for amplification. The recombinant plasmid was sequence confirmed. The recombinant plasmid expressing hsa-miR-133b or empty vector was transfected into SiHa cells and stable cell lines were selected by using puromycin. Over-expression of hsa-miR-133b in SiHa stable cell lines was confirmed by real-time RT-PCR.

Figure 6:
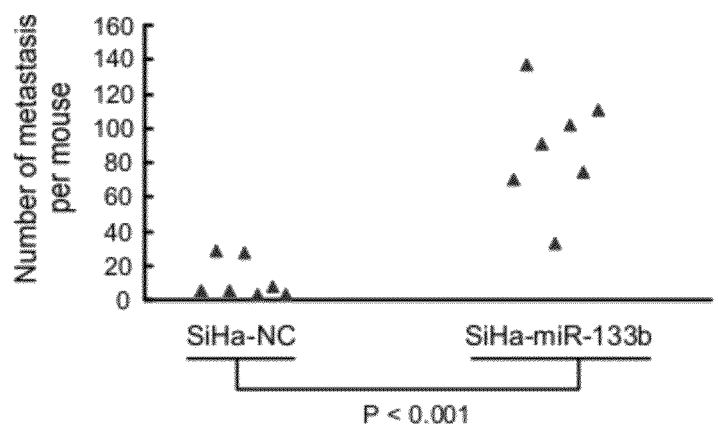
FIG. 6 shows the quantification results of visually observable metastatic foci on lung surface of SCID mice 8 weeks after i.v. injection of SiHa stable cells. SiHa-NC represents SiHa stable cell lines constructed using empty vectors (pCMV-puromycin) as negative control, whereas SiHa-miR-133b represents SiHa stable cell lines constructed using miR-133b-expressing plasmids (pCMV-miR-133b).

To model metastasis, SiHa stable cells over-expressing hsa-miR-133b or control SiHa stable cells (2×10$^6$ cells/mouse) were injected into SCID mice via tail vein injection. Seven mice were used for each stable cell line. All mice were killed at 60 days after injection. To clearly observe the metastasis nodules, the lungs were fixed in Bouin's solution (Sigma) displaying lung tissue as brown and metastatic foci as white nodules. Observable metastatic foci on lung surface were counted. As shown in FIG. 6, SiHa cells over-expressing hsa-miR-133b formed more metastatic tumors in mouse lungs than those formed by control SiHa cells, indicating that hsa-miR-133b promotes metastasis.

REFERENCES

Bandres, E., Cubedo, E., Agirre, X., Malumbres, R., Zarate, R., Ramirez, N., Abajo, A., Navarro, A., Moreno, I., Monzo, M., et al. (2006). Identification by Real-time PCR of 13 mature microRNAs differentially expressed in colorectal cancer and non-tumoral tissues. Mol Cancer 5, 29.

Budhu, A., Jia, H. L., Forgues, M., Liu, C. G., Goldstein, D., Lam, A., Zanetti, K. A., Ye, Q. H., Qin, L. X., Croce, C. M., et al. (2008). Identification of metastasis-related microRNAs in hepatocellular carcinoma. Hepatology 47, 897-907.

Burk, R. D. (1999). Pernicious papillomavirus infection. N. Engl. J. Med. 341, 1687-1688.

Calin, G. A., Sevignani, C., Dumitru, C. D., Hyslop, T., Noch, E., Yendamuri, S., Shimizu, M., Rattan, S., Bullrich, F., Negrini, M., et al. (2004). Human microRNA genes are frequently located at fragile sites and genomic regions involved in cancers. Proc. Natl. Acad. Sci. USA 101, 2999-3004.

Chen, C. Z. (2005). MicroRNAs as oncogenes and tumor suppressors. N. Engl. J. Med. 353, 1768-1771.

Fatica, A., Rosa, A., Fazi, F., Ballarino, M., Morlando, M., De Angelis, F. G., Caffarelli, E., Nervi, C., and Bozzoni, I. (2006). MicroRNAs and hematopoietic differentiation. Cold Spring Harb. Symp. Quant. Biol. 71, 205-210.

Guo, Y., Chen, Z., Zhang, L., Zhou, F., Shi, S., Feng, X., Li, B., Meng, X., Ma, X., Luo, M., et al. (2008). Distinctive microRNA profiles relating to patient survival in esophageal squamous cell carcinoma. Cancer Res. 68, 26-33.

He, L., He, X., Lim, L. P., de Stanchina, E., Xuan, Z., Liang, Y., Xue, W., Zender, L., Magnus, J., Ridzon, D., et al. (2007). A microRNA component of the p53 tumour suppressor network. Nature 447, 1130-1134.

Hwang, H. W., and Mendell, J. T. (2006). MicroRNAs in cell proliferation, cell death, and tumorigenesis. Br. J. Cancer 94, 776-780.

Lee, J. W., Choi, C. H., Choi, J. J., Park, Y. A., Kim, S. J., Hwang, S. Y., Kim, W. Y., Kim, T. J., Lee, J. H., Kim, B. G., et al. (2008). Altered microRNA expression in cervical carcinomas. Clin. Cancer Res. 14, 2535-2542.

Lewis, B. P., Burge, C. B., and Bartel, D. P. (2005). Conserved seed pairing, often flanked by adenosines, indicates that thousands of human genes are microRNA targets. Cell 120, 15-20.

Lewis, B. P., Shih, I. H., Jones-Rhoades, M. W., Bartel, D. P., and Burge, C. B. (2003). Prediction of mammalian microRNA targets. Cell 115, 787-798.

Ma, L., Teruya-Feldstein, J., and Weinberg, R. A. (2007). Tumour invasion and metastasis initiated by microRNA-10b in breast cancer. Nature 449, 682-688.

Parkin, D. M., Bray, F., Ferlay, J., and Pisani, P. (2005). Global cancer statistics, 2002. CA Cancer J. Clin. 55, 74-108.

Scheffner, M., Werness, B. A., Huibregtse, J. M., Levine, A. J., and Howley, P. M. (1990). The E6 oncoprotein encoded by human papillomavirus types 16 and 18 promotes the degradation of p53. Cell 63, 1129-1136.

Szafranska, A. E., Davison, T. S., John, J., Cannon, T., Sipos, B., Maghnouj, A., Labourier, E., and Hahn, S. A. (2007). MicroRNA expression alterations are linked to tumorigenesis and non-neoplastic processes in pancreatic ductal adenocarcinoma. Oncogene 26, 4442-4452.

Varnholt, H., Drebber, U., Schulze, F., Wedemeyer, I., Schirmacher, P., Dienes, H. P., and Odenthal, M. (2008). MicroRNA gene expression profile of hepatitis C virus-associated hepatocellular carcinoma. Hepatology 47, 1223-1232.

Voorhoeve, P. M., le Sage, C., Schrier, M., Gillis, A. J., Stoop, H., Nagel, R., Liu, Y. P., van Duijse, J., Drost, J., Griekspoor, A., et al. (2006). A genetic screen implicates miRNA-372 and miRNA-373 as oncogenes in testicular germ cell tumors. Cell 124, 1169-1181.

Wang, X., Tang, S., Le, S. Y., Lu, R., Rader, J. S., Meyers, C., and Zheng, Z. M. (2008). Aberrant expression of oncogenic and tumor-suppressive microRNAs in cervical cancer is required for cancer cell growth. PLoS ONE 3, e2557.

Wong, T. S., Liu, X. B., Chung-Wai Ho, A., Po-Wing Yuen, A., Wai-Man Ng, R., and Ignace Wei, W. (2008). Identification of pyruvate kinase type M2 as potential oncoprotein in squamous cell carcinoma of tongue through microRNA profiling. Int J Cancer 123, 251-257.

Yekta, S., Shih, I. H., and Bartel, D. P. (2004). MicroRNA-directed cleavage of HOXB8 mRNA. Science 304, 594-596.

zur Hausen, H. (2002). Papillomaviruses and cancer: from basic studies to clinical application. Nat. Rev. Cancer 2, 342-350.

What is claimed is:

1. A system for determining the level of MicroRNA (miRNA) expression, which system comprises a plurality of probes, wherein at least about 50% of the probes are capable of detecting at least one, at least five, at least ten, or all miRNAs having a nucleotide sequence set forth in SEQ ID NO:1-20, wherein at least one of the miRNA comprises hsa-miR-133b, wherein the probes are immobilized on a solid substrate covalently, directly or indirectly, and wherein the system comprises 20 probes having the sequences of:

a) complementary sequences to the nucleotide sequences set forth in SEQ ID NO:1-20; or b) the sequences of a) linked to 10-30 polyT.

2. A method for testing a sample for cervical cancer or cervical dysplasia, which method comprises:
   a) determining the level of miRNA expression in the sample using the system of claim 1;
   b) comparing the level of miRNA expression with a reference level; and
   c) classifying the sample as cancerous or dysplastic if the sample exhibits a characteristic change in the level of miRNA expression.

3. The method of claim 2, wherein the characteristic change in the level of miRNA expression comprises a substantial increase in the level of at least one, at least three, at least five, or all miRNA having a nucleotide sequence that is set forth in SEQ ID NO:1-13, and/or a substantial decrease in the level of at least one, at least three, at least five, or all miRNA having a nucleotide sequence that is set forth in SEQ ID NO:14-20.

4. The method of claim 3, wherein the characteristic change in the level of miRNA expression comprises a substantial increase in the level of hsa-miR-133b.

5. The method of claim 2, wherein the sample comprises cervical tissue, lymph node, blood, or serum.

6. The method of claim 2, wherein the sample is from an individual suspected of having cervical cancer or cervical dysplasia, wherein the cervical cancer is squamous cell cancer or adenocarcinoma.

7. The method of claim 2, wherein the miRNA expression level is determined by Northern blot analysis, in situ hybridization, quantitative RT-PCR, or microarray analysis.

8. A method for testing a sample for cervical cancer or cervical dysplasia, which method comprises determining the genetic status of at least one miRNA in the sample using the system of claim 1, wherein a characteristic change in the genetic status of the miRNA indicates the sample as cancerous or dysplastic.

9. The method of claim 8, wherein the characteristic change in the genetic status of miRNA comprises an increase in copy number of at least one, at least three, at least five, or all miRNA having a nucleotide sequence that is set forth in SEQ ID NO:1-13, and/or a decrease in copy number of at least one, at least three, at least five, or all miRNA having a nucleotide sequence that is set forth in SEQ ID NO:14-20.

10. The method of claim 9, wherein the characteristic change in the genetic status of miRNA comprises an increase in copy number of hsa-miR-133b.

11. The method of claim 8, wherein the sample comprises cervical tissue, lymph node, blood, or serum.

12. The method of claim 8, wherein the sample is from an individual suspected of having cervical cancer or cervical dysplasia, wherein the cervical cancer is squamous cell cancer or adenocarcinoma.

13. The method of claim 8, wherein the genetic status of miRNA is determined by Southern blot analysis, FISH analysis, analysis for loss of heterozygosity, sequencing or microarray analysis.

14. A method for testing a sample for colorectal cancer, tongue squamous cell carcinoma, esophageal squamous cell carcinoma and pancreatic ductal adenocarcinoma, which method comprises:
   a) determining the level of miRNA expression in the sample using the system of claim 1;
   b) comparing the level of miRNA expression with a reference level, and
   c) classifying the sample as cancerous if the sample exhibits a characteristic change in the level of miRNA expression.

15. The method of claim 14, wherein the characteristic change in the level of miRNA expression comprises a substantial change in the level of hsa-miR-133b.

16. The method of claim 14, wherein the sample comprises tissue, lymph node, blood, or serum.

17. The method of claim 14, wherein the miRNA expression level is determined by Northern blot analysis, in situ hybridization, quantitative RT-PCR or microarray analysis.

18. A method for testing a sample for colorectal cancer, tongue squamous cell carcinoma, esophageal squamous cell carcinoma and pancreatic ductal adenocarcinoma, which method comprises determining the genetic status of the miRNA in the sample using the system of claim 1, wherein a characteristic change in the genetic status of the miRNA indicates the sample as cancerous.

19. The method of claim 18, wherein the characteristic change in the genetic status of miRNA comprises a substantial change in copy number of hsa-miR-133.

20. The method of claim 18, wherein the genetic status of miRNA is determined by Southern blot analysis, FISH analysis, analysis for loss of heterozygosity, sequencing or microarray analysis.

21. The system of claim 1, wherein the probes are at least 10 or at least 20 nucleotides in length.

22. The system of claim 1, wherein at least about 50% of the probes are capable of detecting an miRNA having a nucleotide sequence set forth in SEQ ID NO: 1-13.

23. The system of claim 1, wherein at least about 50% of the probes are capable of detecting an miRNA having a nucleotide sequence set forth in SEQ ID NO: 14-20.

24. The system of claim 1, wherein at least about 50% of the probes are capable of detecting an miRNA having a nucleotide sequence set forth in SEQ ID NO: 1-13 and an miRNA having a nucleotide sequence set forth in SEQ ID NO: 14-20.

* * * * *

SEQUENCE LISTING

```
<160> NUMBER OF SEQ ID NOS: 29

<210> SEQ ID NO 1
<211> LENGTH: 22
<212> TYPE: RNA
<213> ORGANISM: Artificial Sequence
<220> FEATURE:
<223> OTHER INFORMATION: synthetic construct

<400> SEQUENCE: 1 uuugguccc uucaaccagc ug                                                  22

<210> SEQ ID NO 2
<211> LENGTH: 22
<212> TYPE: RNA
<213> ORGANISM: Artificial Sequence
<220> FEATURE:
<223> OTHER INFORMATION: synthetic construct

<400> SEQUENCE: 2 uuugguccc uucaaccagc ua                                                  22

<210> SEQ ID NO 3
<211> LENGTH: 21
<212> TYPE: RNA
<213> ORGANISM: Artificial Sequence
<220> FEATURE:
<223> OTHER INFORMATION: synthetic construct

<400> SEQUENCE: 3
uaccacaggg uagaaccacg g                                                  21

<210> SEQ ID NO 4
<211> LENGTH: 22
<212> TYPE: RNA
<213> ORGANISM: Artificial Sequence
```

```
<220> FEATURE:
<223> OTHER INFORMATION: synthetic construct

<400> SEQUENCE: 4
ggugcagugc ugcaucucug gu                                    22

<210> SEQ ID NO 5
<211> LENGTH: 23
<212> TYPE: RNA
<213> ORGANISM: Artificial Sequence
<220> FEATURE:
<223> OTHER INFORMATION: synthetic construct

<400> SEQUENCE: 5
guccaguuuu cccaggaauc ccu                                   23

<210> SEQ ID NO 6
<211> LENGTH: 22
<212> TYPE: RNA
<213> ORGANISM: Artificial Sequence
<220> FEATURE:
<223> OTHER INFORMATION: synthetic construct

<400> SEQUENCE: 6
ugucaguuug ucaaauaccc ca                                    22

<210> SEQ ID NO 7
<211> LENGTH: 22
<212> TYPE: RNA
<213> ORGANISM: Artificial Sequence
<220> FEATURE:
<223> OTHER INFORMATION: synthetic construct

<400> SEQUENCE: 7
cacccguaga accgaccuug cg                                    22

<210> SEQ ID NO 8
<211> LENGTH: 23
<212> TYPE: RNA
<213> ORGANISM: Artificial Sequence
<220> FEATURE:
<223> OTHER INFORMATION: synthetic construct

<400> SEQUENCE: 8
agcuacauug ucugcugggu uuc                                   23

<210> SEQ ID NO 9
<211> LENGTH: 22
<212> TYPE: RNA
<213> ORGANISM: Artificial Sequence
<220> FEATURE:
<223> OTHER INFORMATION: synthetic construct

<400> SEQUENCE: 9
aaaagcuggg uugagagggc ga                                    22

<210> SEQ ID NO 10
<211> LENGTH: 22
<212> TYPE: RNA
<213> ORGANISM: Artificial Sequence
<220> FEATURE:
<223> OTHER INFORMATION: synthetic construct

<400> SEQUENCE: 10
aacccguaga uccgaacuug ug                                    22
```

```
<210> SEQ ID NO 11
<211> LENGTH: 23
<212> TYPE: RNA
<213> ORGANISM: Artificial Sequence
<220> FEATURE:
<223> OTHER INFORMATION: synthetic construct

<400> SEQUENCE: 11
cccaguguuc agacuaccug uuc                                              23

<210> SEQ ID NO 12
<211> LENGTH: 22
<212> TYPE: RNA
<213> ORGANISM: Artificial Sequence
<220> FEATURE:
<223> OTHER INFORMATION: synthetic construct

<400> SEQUENCE: 12
ucggauccgu cugagcuugg cu                                               22

<210> SEQ ID NO 13
<211> LENGTH: 22
<212> TYPE: RNA
<213> ORGANISM: Artificial Sequence
<220> FEATURE:
<223> OTHER INFORMATION: synthetic construct

<400> SEQUENCE: 13
acagcaggca cagacaggca gu                                               22

<210> SEQ ID NO 14
<211> LENGTH: 22
<212> TYPE: RNA
<213> ORGANISM: Artificial Sequence
<220> FEATURE:
<223> OTHER INFORMATION: synthetic construct

<400> SEQUENCE: 14
gugaaauguu uaggaccacu ag                                               22

<210> SEQ ID NO 15
<211> LENGTH: 22
<212> TYPE: RNA
<213> ORGANISM: Artificial Sequence
<220> FEATURE:
<223> OTHER INFORMATION: synthetic construct

<400> SEQUENCE: 15
ugauauguuu gauauauuag gu                                               22

<210> SEQ ID NO 16
<211> LENGTH: 22
<212> TYPE: RNA
<213> ORGANISM: Artificial Sequence
<220> FEATURE:
<223> OTHER INFORMATION: synthetic construct

<400> SEQUENCE: 16
uaauacugcc ugguaaugau ga                                               22

<210> SEQ ID NO 17
<211> LENGTH: 23
<212> TYPE: RNA
<213> ORGANISM: Artificial Sequence
<220> FEATURE:
<223> OTHER INFORMATION: synthetic construct
```

-continued

```
<400> SEQUENCE: 17
uaauacugcc ggguaaugau gga                                         23

<210> SEQ ID NO 18
<211> LENGTH: 22
<212> TYPE: RNA
<213> ORGANISM: Artificial Sequence
<220> FEATURE:
<223> OTHER INFORMATION: synthetic construct

<400> SEQUENCE: 18
uaacacuguc ugguaacgau gu                                          22

<210> SEQ ID NO 19
<211> LENGTH: 21
<212> TYPE: RNA
<213> ORGANISM: Artificial Sequence
<220> FEATURE:
<223> OTHER INFORMATION: synthetic construct

<400> SEQUENCE: 19
aggcaagaug cuggcauagc u                                           21

<210> SEQ ID NO 20
<211> LENGTH: 22
<212> TYPE: RNA
<213> ORGANISM: Artificial Sequence
<220> FEATURE:
<223> OTHER INFORMATION: synthetic construct

<400> SEQUENCE: 20
uaacacuguc ugguaaagau gg                                          22

<210> SEQ ID NO 21
<211> LENGTH: 29
<212> TYPE: DNA
<213> ORGANISM: Artificial Sequence
<220> FEATURE:
<223> OTHER INFORMATION: synthetic construct

<400> SEQUENCE: 21
gcggcggtgc tttgctagag ctggtaaaa                                   29

<210> SEQ ID NO 22
<211> LENGTH: 26
<212> TYPE: DNA
<213> ORGANISM: Artificial Sequence
<220> FEATURE:
<223> OTHER INFORMATION: synthetic construct

<400> SEQUENCE: 22
cggcggagct acagctggtt gaaggg                                      26

<210> SEQ ID NO 23
<211> LENGTH: 25
<212> TYPE: DNA
<213> ORGANISM: Artificial Sequence
<220> FEATURE:
<223> OTHER INFORMATION: synthetic construct

<400> SEQUENCE: 23
cgcggctgct ctggctggtc aaacg                                       25

<210> SEQ ID NO 24
```

```
<211> LENGTH: 26
<212> TYPE: DNA
<213> ORGANISM: Artificial Sequence
<220> FEATURE:
<223> OTHER INFORMATION: synthetic construct

<400> SEQUENCE: 24
cggcggtcag gaagacggac ttggtt                                        26

<210> SEQ ID NO 25
<211> LENGTH: 20
<212> TYPE: DNA
<213> ORGANISM: Artificial Sequence
<220> FEATURE:
<223> OTHER INFORMATION: synthetic construct

<400> SEQUENCE: 25
aacgcttcac gaatttgcgt                                               20

<210> SEQ ID NO 26
<211> LENGTH: 17
<212> TYPE: DNA
<213> ORGANISM: Artificial Sequence
<220> FEATURE:
<223> OTHER INFORMATION: synthetic construct

<400> SEQUENCE: 26
ctcgcttcgg cagcaca                                                  17

<210> SEQ ID NO 27
<211> LENGTH: 20
<212> TYPE: DNA
<213> ORGANISM: Artificial Sequence
<220> FEATURE:
<223> OTHER INFORMATION: synthetic construct

<400> SEQUENCE: 27
aacgcttcac gaatttgcgt                                               20

<210> SEQ ID NO 28
<211> LENGTH: 40
<212> TYPE: DNA
<213> ORGANISM: Artificial Sequence
<220> FEATURE:
<223> OTHER INFORMATION: synthetic construct

<400> SEQUENCE: 28
ctgacaggat ccgtaagagg acattctgga caaggcaagc                         40

<210> SEQ ID NO 29
<211> LENGTH: 40
<212> TYPE: DNA
<213> ORGANISM: Artificial Sequence
<220> FEATURE:
<223> OTHER INFORMATION: synthetic construct

<400> SEQUENCE: 29
cgcacgaatt cattcctggg agcataagaa tatggtgaaa                         40
```